(12) United States Patent
Cordatos et al.

(10) Patent No.: US 11,981,436 B2
(45) Date of Patent: May 14, 2024

(54) PERSONAL AIRCRAFT SEAT AIR TREATMENT SYSTEM

(71) Applicant: B/E Aerospace, Inc., Winston-Salem, NC (US)

(72) Inventors: Haralambos Cordatos, Colchester, CT (US); Catherine Thibaud, South Windsor, CT (US); Brian St. Rock, Andover, CT (US); Michael Fortin, Andover, CT (US); Brian M. Welch, West Hartford, CT (US); Matthew R. Pearson, Hartford, CT (US); Mathieu Le Cam, Cobh (IE)

(73) Assignee: B/E Aerospace, Inc., Winston-Salem, NC (US)

( * ) Notice: Subject to any disclaimer, the term of this patent is extended or adjusted under 35 U.S.C. 154(b) by 442 days.

(21) Appl. No.: 17/343,328

(22) Filed: Jun. 9, 2021

(65) Prior Publication Data

US 2021/0387731 A1    Dec. 16, 2021

Related U.S. Application Data

(60) Provisional application No. 63/080,252, filed on Sep. 18, 2020, provisional application No. 63/037,444, filed on Jun. 10, 2020.

(51) Int. Cl.
| | |
|---|---|
| *B64D 11/06* | (2006.01) |
| *A61L 9/20* | (2006.01) |
| *B64D 13/06* | (2006.01) |

(52) U.S. Cl.
CPC ........... *B64D 11/0626* (2014.12); *A61L 9/20* (2013.01); *B64D 13/06* (2013.01); *B64D 2013/0655* (2013.01)

(58) Field of Classification Search
USPC .......................................................... 454/76
See application file for complete search history.

(56) References Cited

U.S. PATENT DOCUMENTS

| | | | |
|---|---|---|---|
| 4,435,025 A | 3/1984 | Weintraub | |
| 5,114,382 A * | 5/1992 | Steiner | B64D 15/02 |
| | | | 454/76 |

(Continued)

FOREIGN PATENT DOCUMENTS

| | | |
|---|---|---|
| CN | 204709594 U | 10/2015 |
| CN | 106267508 B | 10/2018 |

(Continued)

OTHER PUBLICATIONS

Extended Search Report for European Application No. 21178834.4 dated Nov. 2, 2021, 8 pages.

(Continued)

*Primary Examiner* — Ko-Wei Lin
(74) *Attorney, Agent, or Firm* — Suiter Swantz IP

(57) ABSTRACT

A personal aircraft seat air treatment system may include an air blower, a ventilation output component installed within a passenger compartment, and a treatment component fluidically coupled to the air blower and the ventilation output component. The air blower may be configured to receive cabin air from a cabin air ventilation system installed in an aircraft cabin. The ventilation output component may be configured to provide treated air to a breathing area of a passenger proximate to an aircraft seat installed in the passenger compartment. The treatment component may be fluidically coupled to the air blower and the ventilation output component. The treatment component may be configured to receive the cabin air from the air blower and treat the cabin air to generate the treated air.

13 Claims, 18 Drawing Sheets

(56) References Cited

U.S. PATENT DOCUMENTS

| | | | |
|---|---|---|---|
| 5,160,517 A | 11/1992 | Hicks et al. | |
| 7,264,649 B1 | 9/2007 | Johnson et al. | |
| 8,137,436 B2 | 3/2012 | Calis et al. | |
| 10,029,797 B2 | 7/2018 | Space et al. | |
| 2002/0011071 A1* | 1/2002 | Needham | B60N 2/5635 |
| | | | 297/180.13 |
| 2004/0224144 A1 | 11/2004 | Saari et al. | |
| 2011/0240795 A1* | 10/2011 | Brugger | B64D 41/00 |
| | | | 244/58 |
| 2013/0040546 A1* | 2/2013 | Noske | B64D 11/0647 |
| | | | 454/76 |
| 2014/0179212 A1* | 6/2014 | Space | B60N 2/5635 |
| | | | 454/76 |
| 2016/0000960 A1* | 1/2016 | Soares Pinheiro Lopes | |
| | | | B01D 53/8687 |
| | | | 422/121 |
| 2016/0214723 A1* | 7/2016 | Fox | B64D 13/06 |
| 2016/0318613 A1* | 11/2016 | Ludvik | B01D 53/0462 |
| 2017/0283075 A1 | 10/2017 | Garing et al. | |
| 2018/0065752 A1* | 3/2018 | Franco | B64D 13/06 |
| 2019/0161196 A1* | 5/2019 | Heuer | B64D 13/06 |
| 2021/0188446 A1* | 6/2021 | Christenson | B64D 13/04 |
| 2021/0361815 A1* | 11/2021 | Krosney | A61L 9/20 |
| 2021/0370212 A1* | 12/2021 | Misawa | B64D 11/0626 |

FOREIGN PATENT DOCUMENTS

| | | |
|---|---|---|
| GB | 1120179 A | 7/1968 |
| WO | 2007147259 A1 | 12/2007 |

OTHER PUBLICATIONS

Cigars International, "HUMI-CARE Bead Gel Humidifiction", URL: https://www.cigarsinternational.com/p/humi-care-bead-gel-humidification-humidification/1438271/, Downloaded May 14, 2020, 1 page.

Materials World Magazine, Nov. 2, 2013, "Healthcare on the Cheap—Innovations From Appropriate Healthcare Technologies Event", URL: https://www.iom3.org/materials-world-magazine/news/2013/nov/02/healthcare-cheap-innovations-appropriate-healthcare?c=574.

* cited by examiner

PERSONAL AIRCRAFT SEAT AIR TREATMENT SYSTEM

CROSS-REFERENCE TO RELATED APPLICATIONS

The present application is related to and claims benefit of the earliest available effective filing date from the following applications: the present application claims the benefit of U.S. Provisional Application Ser. No. 63/037,444, filed Jun. 10, 2020 and U.S. Provisional Application Ser. No. 63/080,252, filed Sep. 18, 2020, which are each incorporated herein by reference in the entirety.

BACKGROUND

Due to a perceived role of commercial airlines in the spread of viruses and other diseases around the globe, along with possible decisions made with respect to the operating of existing cabin air ventilation systems, there is an increase of concern for a safer and healthier aircraft environment. To promote a generation of the safer and healthier aircraft environment, airlines may desire to provide treated air solutions to passengers and crew members, where the treated air solutions replace or supplement existing cabin air ventilation systems.

SUMMARY

A personal aircraft seat air treatment system is disclosed, in accordance with one or more embodiments of the present disclosure. The air treatment system may include an air blower. The air blower may be configured to receive cabin air from a cabin air ventilation system installed in an aircraft cabin. The cabin air may include a mixture of recirculated air from inside the aircraft cabin and fresh air from outside the aircraft cabin. The air treatment system may include at least one ventilation output component installed within a passenger compartment. The at least one ventilation output component may be configured to provide treated air to at least one breathing area of a passenger. The at least one breathing area may be proximate to an aircraft seat installed in the passenger compartment. The air treatment system may include at least one treatment component fluidically coupled to the air blower and the at least one ventilation output component. The at least one treatment component may be configured to receive at least a portion of the cabin air from the air blower and treat the at least a portion of the cabin air to generate the treated air.

In some embodiments, the at least one treatment component may include an air purifier.

In some embodiments, the air purifier may include an ultraviolet germicidal irradiation lamp. The ultraviolet germicidal irradiation lamp may be configured to generate the treated air from the cabin air by treating the at least a portion of the cabin air received via the air blower with ultraviolet light.

In some embodiments, the at least one ventilation output component may include a plurality of ventilation output components. A first subset of the plurality of ventilation output components may be fluidically coupled to the air purifier and configured to receive the treated air from the air purifier. A second subset of the plurality of ventilation output components may be configured to receive at least a second portion of the cabin air.

In some embodiments, the at least one ventilation output component may include a plurality of ventilation output components. Each ventilation output component of the plurality of ventilation output components may be fluidically coupled to the air purifier and configured to receive the treated air from the purifier.

In some embodiments, the at least one treatment component may include a hydrogel cartridge. The hydrogel cartridge may be configured to generate humidified air from the cabin air by humidifying the at least a portion of the cabin air received from the air blower via dehydration of the hydrogel cartridge.

In some embodiments, the hydrogel cartridge may be configured to be housed within a cannister. The cannister may be fluidically coupled to the air blower and the at least one ventilation output component.

In some embodiments, the cannister may include a main body and a cannister lid. The hydrogel cartridge may be removable from the main body when the cannister lid is disengaged.

In some embodiments, the air treatment system may include an air mixer. The air mixer may be configured to combine the humidified air and at least a second portion of the cabin air to generate the treated air.

In some embodiments, the at least one ventilation output component may include a nozzle.

In some embodiments, the nozzle may be positioned within a head rest, a seat back, or a seat pan of the aircraft seat.

In some embodiments, the air treatment system may include an output blower. The output blower may be configured to receive the treated air and provide the treated air to the at least one breathing area of the passenger.

In some embodiments, the air treatment system may include one or more temperature-adjusting components. The one or more temperature-adjusting components may be configured to adjust the temperature of one or more of the cabin air or the treated air.

An aircraft cabin is disclosed, in accordance with one or more embodiments of the present disclosure. The aircraft cabin may include a cabin air ventilation system. The cabin air ventilation system may be configured to generate cabin air. The cabin air may include a mixture of recirculated air from inside the aircraft cabin and fresh air from outside the aircraft cabin. The aircraft cabin may include a passenger compartment including an aircraft seat and a personal aircraft seat air treatment system. The personal aircraft seat air treatment system may include an air blower. The air blower may be configured to receive the cabin air from the cabin air ventilation system. The personal aircraft seat air treatment system may include at least one ventilation output component installed within the passenger compartment. The at least one ventilation output component may be configured to provide treated air to at least one breathing area of a passenger. The at least one breathing area may be proximate to the aircraft seat installed in the passenger compartment. The personal aircraft seat air treatment system may include at least one treatment component fluidically coupled to the air blower and the at least one ventilation output component. The at least one treatment component may be configured to receive at least a portion of the cabin air from the air blower and treat the at least a portion of the cabin air to generate the treated air.

In some embodiments, the passenger compartment may include a control device. The control device may include one or more processors and memory. The memory may be configured to store a set of program instructions. The one or more processors may be configured to execute the program instructions to adjust one or more parameters of the personal aircraft seat air treatment system. The passenger compartment may include one or more sensors. The one or more sensors may be configured to monitor at least one of rate of airflow or air quality through the personal aircraft seat air treatment system. The one or more sensors may be communicatively coupled to the control device.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are examples and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION OF THE INVENTION

Figure 1A:
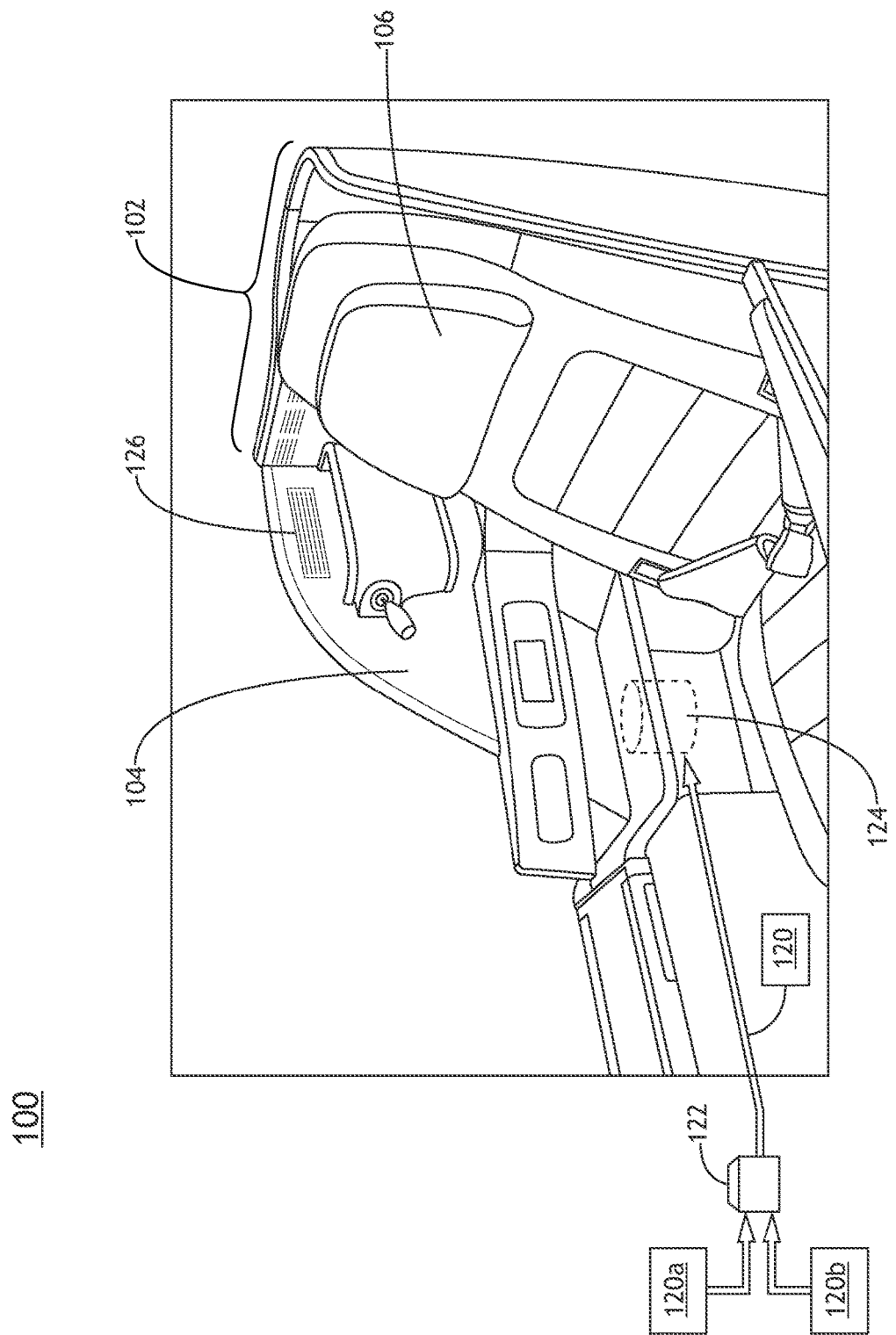
FIG. 1A illustrates a perspective isometric view of an aircraft passenger compartment, according to one or more embodiments of the present disclosure.
Figure 1B:
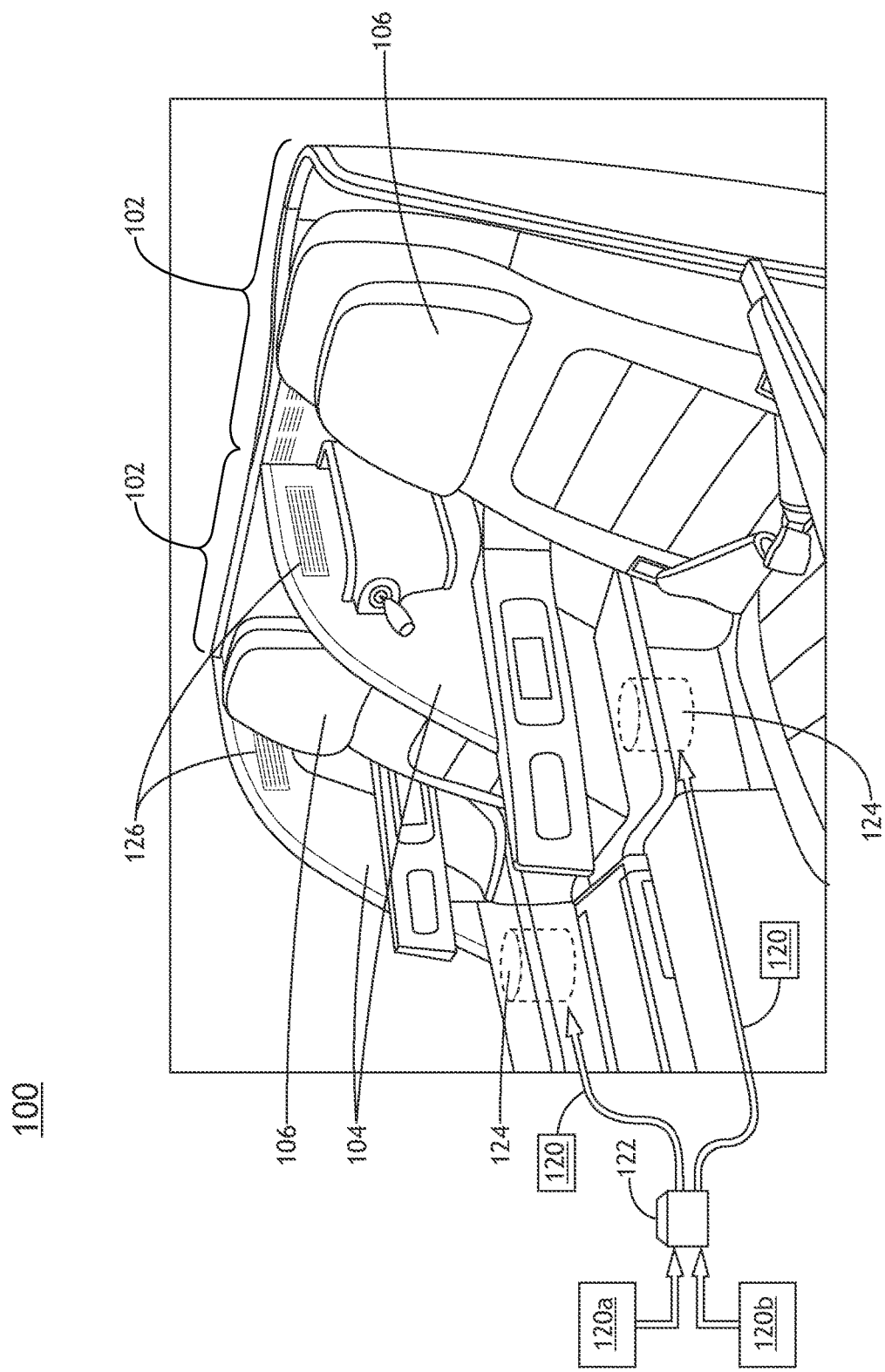
FIG. 1B illustrates a perspective isometric view of multiple aircraft passenger compartments, according to one or more embodiments of the present disclosure.
Figure 1C:
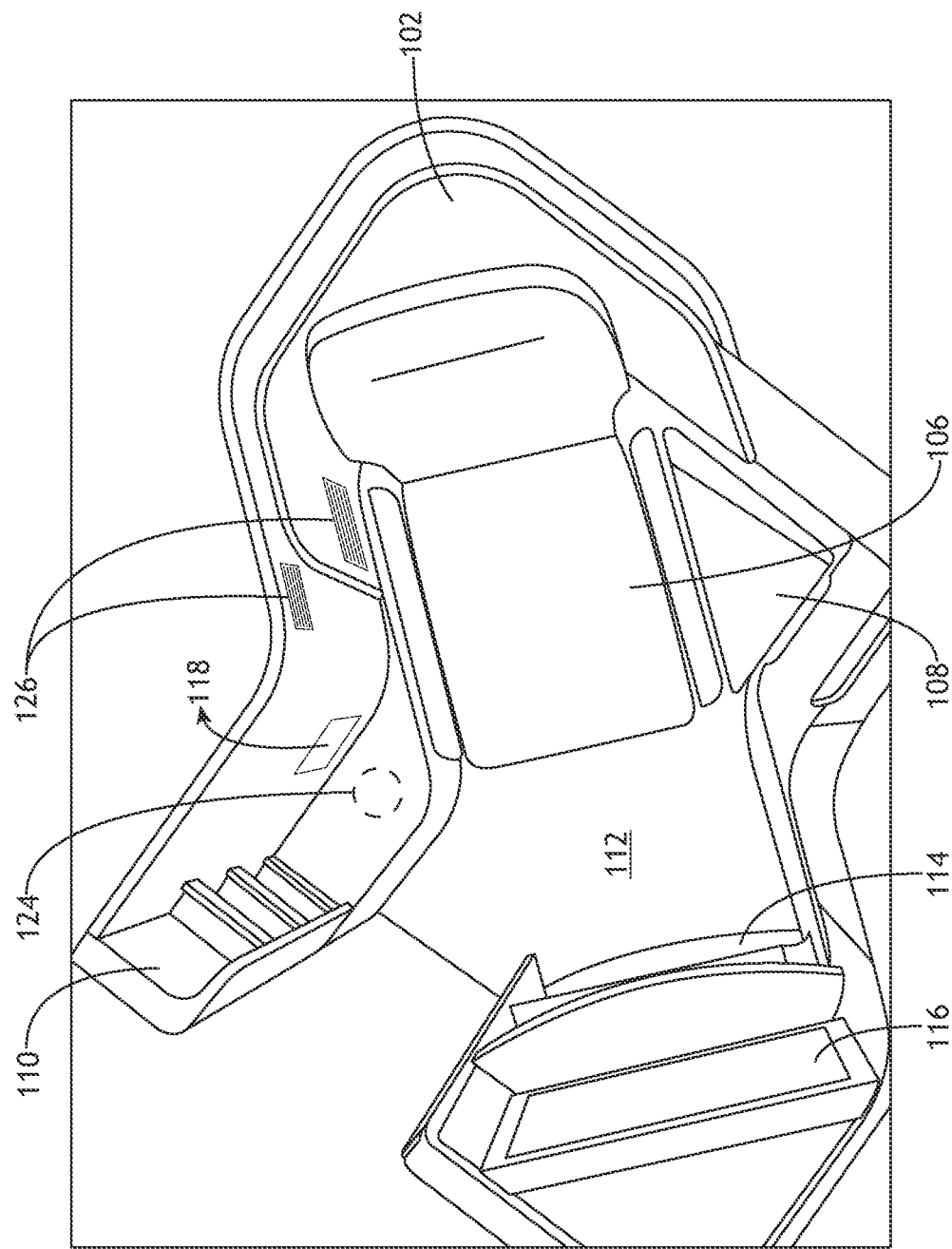
FIG. 1C illustrates a perspective top view of an aircraft passenger compartment, according to one or more embodiments of the present disclosure.
Figure 1D:
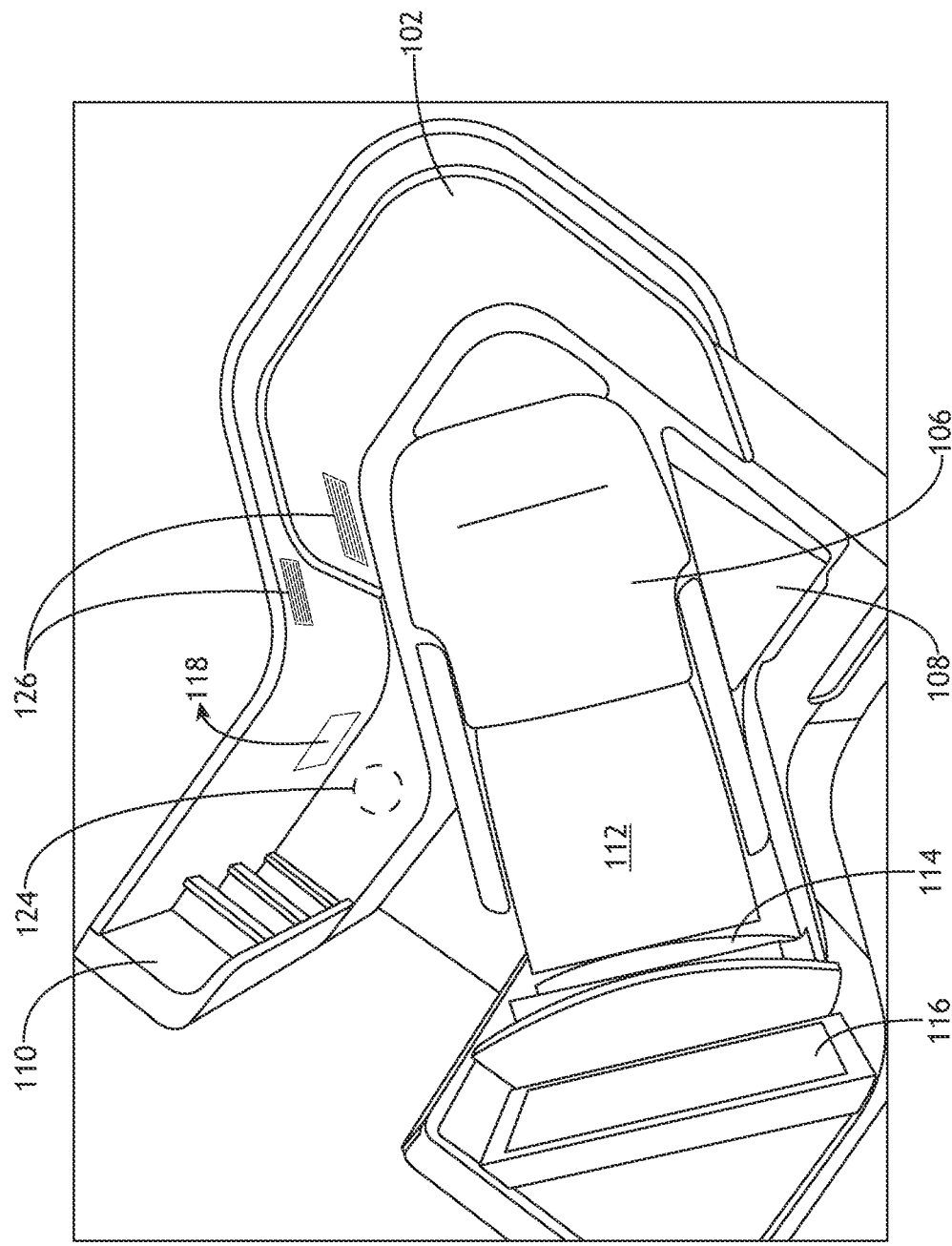
FIG. 1D illustrates a perspective top view of an aircraft passenger compartment, according to one or more embodiments of the present disclosure.
Figure 2A:
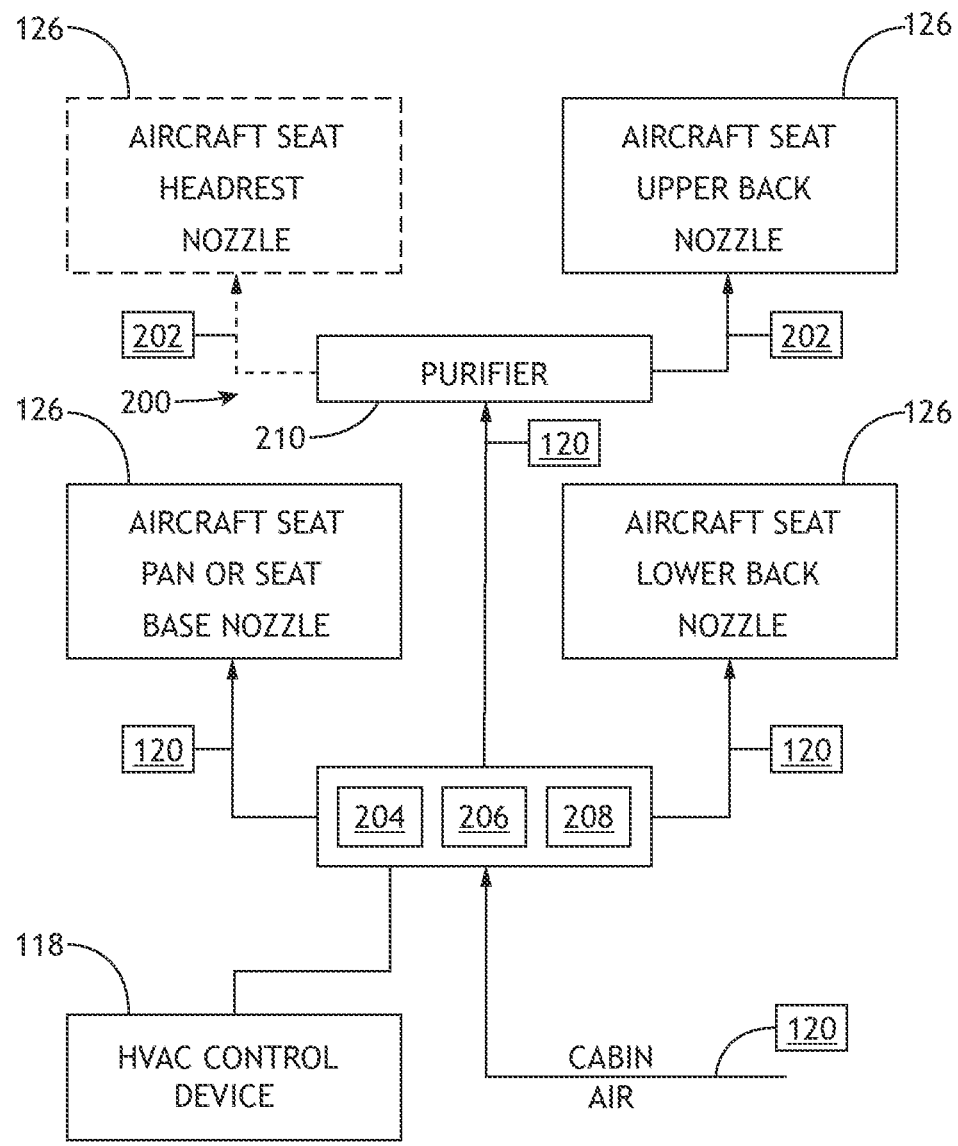
FIG. 2A is a block diagram schematic illustrating a personal aircraft seat air treatment system, in accordance with one or more embodiments of the present disclosure.
Figure 2B:
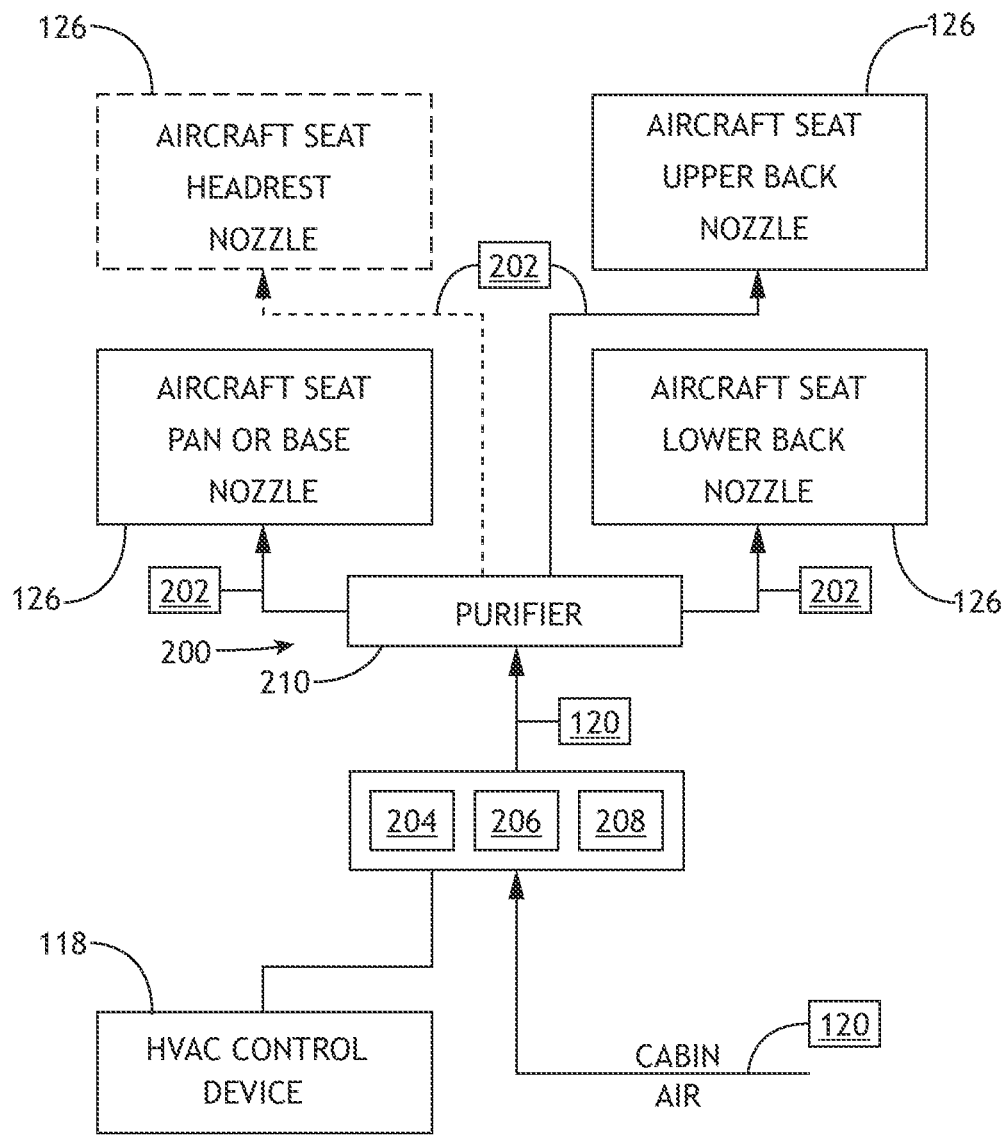
FIG. 2B is a block diagram schematic illustrating a personal aircraft seat air treatment system, in accordance with one or more embodiments of the present disclosure.
Figure 2C:
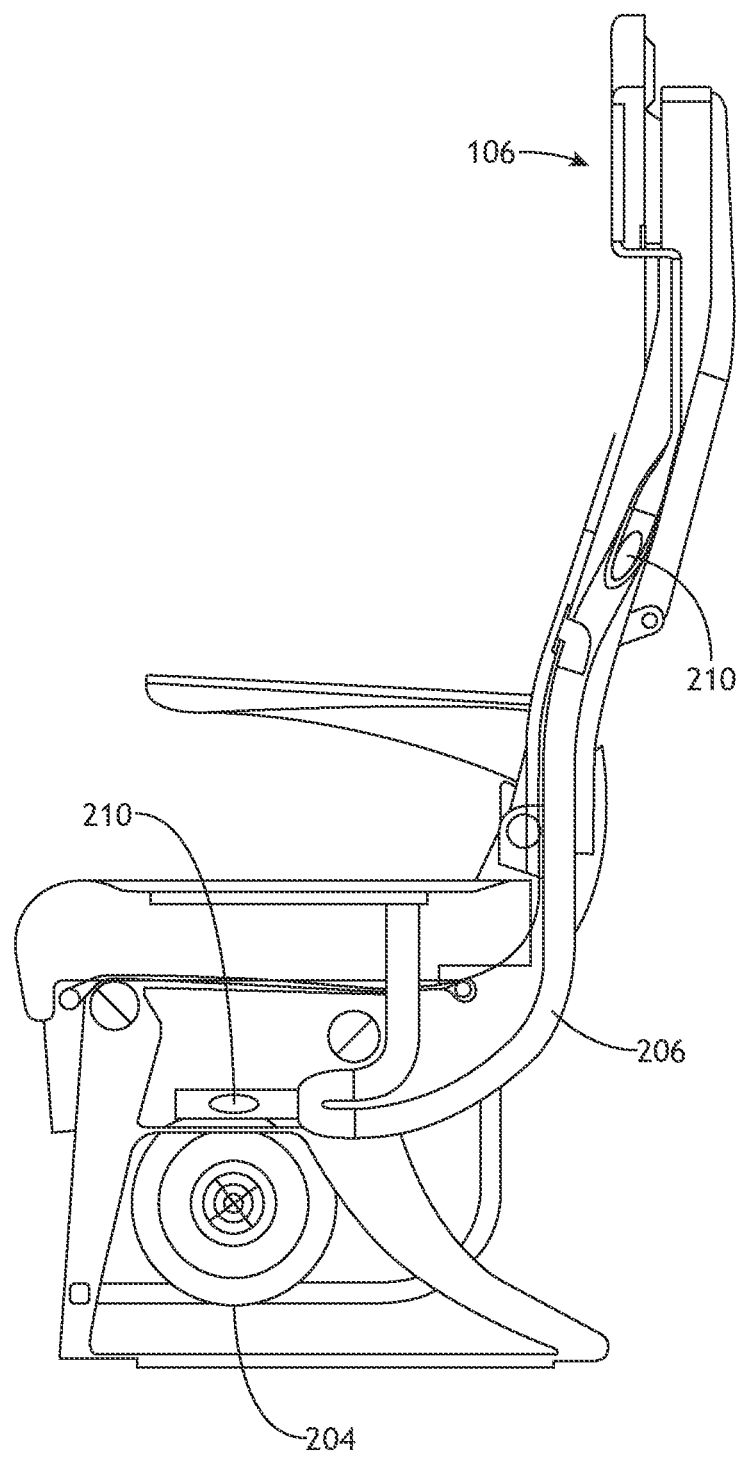
FIG. 2C illustrates a side view of an aircraft three-seat row including a personal air treatment system, in accordance with one or more embodiments of the present disclosure.
Figure 2D:
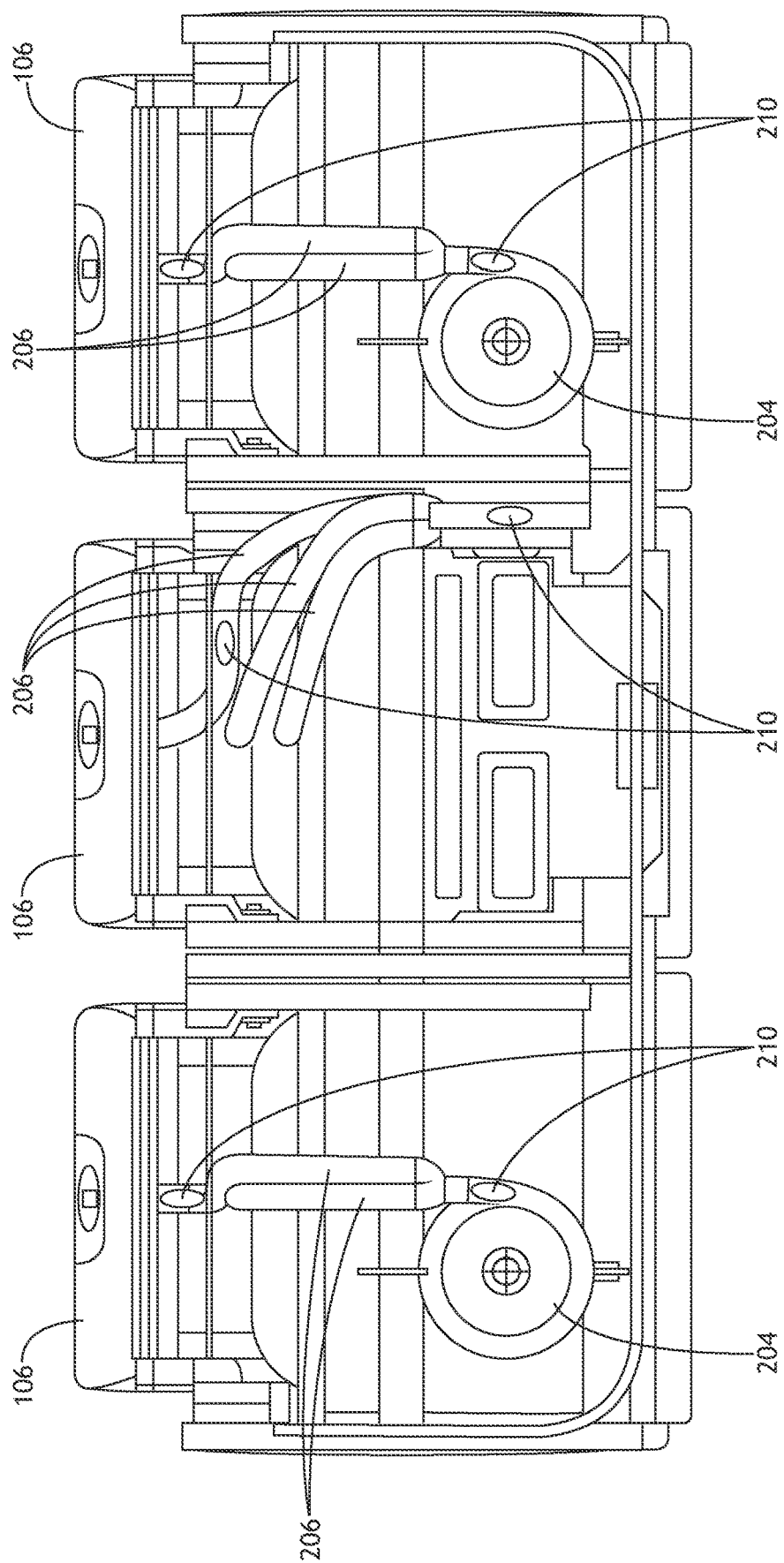
FIG. 2D illustrates a bottom view of an aircraft three-seat row including a personal air treatment system, in accordance with one or more embodiments of the present disclosure.
Figure 2E:
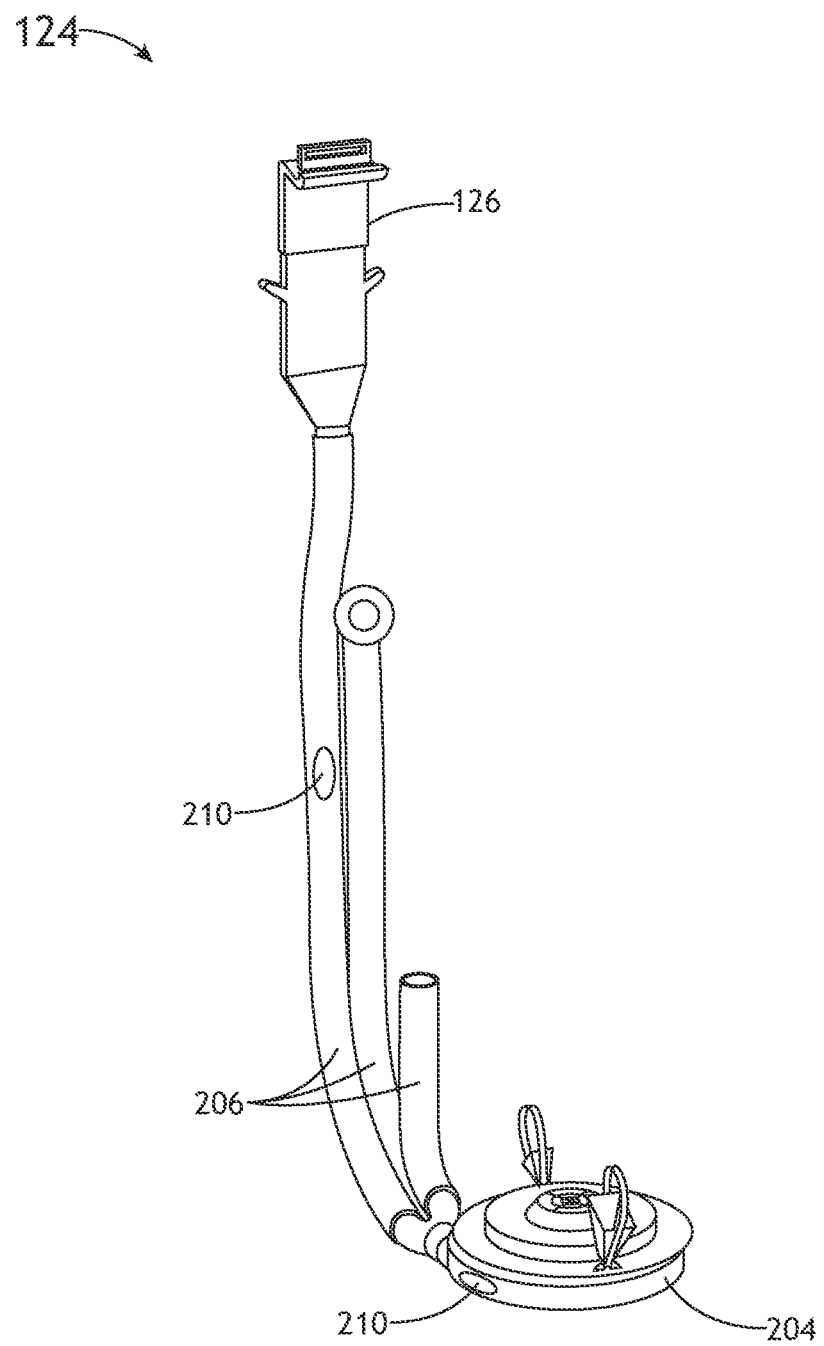
FIG. 2E illustrates a personal aircraft seat air treatment system, in accordance with one or more embodiments of the present disclosure.

Reference will now be made in detail to the subject matter disclosed, which is illustrated in the accompanying drawings.

Before explaining one or more embodiments of the present disclosure in detail, it is to be understood the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the present disclosure. However, it will be apparent to one of ordinary skill in the art having the benefit of the instant disclosure the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), or both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious it is meant otherwise.

Finally, as used herein any reference to "one embodiment" or "some embodiments" means a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination of or sub-combination of two or more such features, along with any other features which may not necessarily be expressly described or inherently present in the instant disclosure.

FIGS. 1A-6 in general illustrate a personal aircraft seat air treatment system, in accordance with one or more embodiments of the present disclosure.

In some embodiments, an aircraft cabin 100 may include one or more aircraft interior structures. For example, the aircraft interior structures may include, but are not limited to, one or more passenger compartments 102. At least some of the one or more aircraft interior structures may be separately-constructed and separately-installed within the aircraft cabin 100. It is noted herein, however, at least some of the one or more aircraft interior structures may be integrated and/or coupled together during installation within the aircraft cabin 100.

In some embodiments, the one or more passenger compartments 102 includes a divider wall 104 with one or more divider wall elements. For example, a wall of the aircraft cabin 100 may be considered a divider wall element of the divider wall 104. By way of another example, at least some of the one or more divider wall elements of the divider wall 104 may be shared between adjacent passenger compartments 102.

A divider wall 104 of the passenger compartment 102 may include an opening into the passenger compartment 102, where the opening is configured to allow entrance into an aircraft aisle of the aircraft cabin 100. The passenger compartment 102 may include a door for the opening. For example, the door may swing or slide into an open position against the divider wall 104. By way of another example, the divider wall 104 may be at least partially hollow, and the door may be slid into a cavity defined by the divider wall 104.

In some embodiments, the one or more passenger compartments 102 each include an aircraft seat 106 (e.g., a business class or first-class passenger seat) and one or more auxiliary monuments 108. It is noted herein the terms "aircraft seat" and "passenger seat" may be considered equivalent, for purposes of the present disclosure.

The one or more passenger compartments 102 may bounded at least in part by one or more aircraft aisles, a divider wall 104, a housed aircraft seat 106 and/or one or more additional passenger compartments 102 and within the aircraft cabin 100. It is noted, however, the passenger compartment 102 may not be limited only to these bounded elements. In addition, the passenger compartment 102 may be implemented adjacent to rows of aircraft seats 106 including two or more additional aircraft seats 106, or the like.

The aircraft seat 106 may include, but are not limited to, some combination of seat pans, seat backs, headrests, seat cushions, diaphragms, dress covers, legs, support members, actuatable armrests, seatbelts, or the like. The aircraft seat 106 may be attachable to embedded seat tracks located in a floor of the aircraft cabin 100 via conventional track fasteners and/or be couplable to the passenger compartment 102 (e.g., where the passenger compartment 102 may be attachable to embedded seat tracks located in the floor of the aircraft cabin 100 via conventional track fasteners).

The aircraft seat 106 may be translatable (e.g., trackable or slidable). The aircraft seat 106 may be rotated about one or more axes. For example, the aircraft seat 106 may be rotatable about an axis cross-wise through the aircraft seat 106 into a position including, but not limited to, an upright or raised position (e.g., as illustrated in at least FIGS. 1A and 1B), one or more lounge or reclined positions (e.g., as illustrated in at least FIG. 1C), and/or a lie-flat or bed position (e.g., as illustrated in at least FIG. 1D). By way of another example, the aircraft seat 106 may be rotatable about a vertical axis (e.g., swivelable). The aircraft seat 106 may be fully positionable between outer limits of motion as defined by the moveable components of the aircraft seat 106, the divider wall 104, and/or auxiliary monuments in the passenger compartment 102.

The aircraft seat 106 may be fully positionable between the outer limits of motion as defined by the moveable components of the aircraft seat 106 and/or the one or more auxiliary monuments 108 of the passenger compartment 102. It is noted herein an upright or raised position may be considered a taxi, takeoff, or landing (TTL) position during select stages of flight (though the upright or raised position is not limited to use during the select stages of flight as the TTL position, but also may be used at any point during the flight), for purposes of the present disclosure. In addition, it is noted herein that any position that does not meet the above-defined requirements of the TTL position may be considered a non-TTL position, for purposes of the present disclosure. Further, it is noted herein the aircraft seat 106 may be actuatable (e.g., translatable and/or rotatable) from the TTL position to a non-TTL position, and/or vice versa. Further, it is noted herein the aircraft seat 106 may be capable of a fully upright or raised position, and that the TTL position may have a more reclined seat back cushion and a more angled upward seat pan cushion as compared to the fully upright or raised position. Therefore, the above description should not be interpreted as a limitation on the present disclosure but merely an illustration.

The aircraft seat 106 may be configured to avoid contact with the one or more auxiliary monuments 108 when transitioning between positions (e.g., between the upright or raised position and the lie-flat or bed position). It is noted herein that at least some components (e.g., the divider wall 104 with one or more divider wall elements such as the one or more auxiliary monuments 108, or the like) may conform to a portion of an aircraft seat 106. In this regard, the amount of floor area of the aircraft cabin 100 necessary for the one or more aircraft seats 106 may be reduced.

The one or more auxiliary monuments 108 may include, but are not limited to, a structure with a horizontal (or substantially horizontal) surface such as a tray or table, a side stand, or the like. The structure may include a top surface, a bottom surface, and/or one or more side surfaces. For example, a structure may include a single continuous side surface where all corners are rounded. By way of another example, the structure may include up to an N number of side surfaces where the auxiliary monument includes up to an N number of corners. The structure may be actuatable (e.g., may extend a select distance from a stored position to an extended position proximate to a passenger, similar to an aircraft tray table). It is noted herein, however, that the structure may be fixed in position.

In some embodiments, the divider wall 104 and/or the one or more auxiliary monuments 108 includes a defined cavity for use as a storage compartment 110.

For example, the storage compartment 110 may be configured to receive and hold (e.g., contain, secure, or the like) one or more passenger amenities including, but not limited to, paper-printed materials (e.g., magazines, newspapers, pamphlets, or the like), select personal electronic devices (e.g., phones, tablets, phablets, laptops, music devices, digital video disc (DVD) players, handheld gaming consoles or devices, or the like), food products, drink products, or the like.

By way of another example, the storage compartment 110 may include one or more electronic connections for one or more passenger amenities such as, but not limited to, one or more charging ports, one or more charging cables, or the like.

By way of another example, the storage compartment 110 may include one or more electronic connections in communication with one or more components of the passenger compartment 102 such as, but not limited to, one or more display device connection ports, one or more display device connection cables, one or more audio output jacks (e.g., headphone jacks), one or more audio input jacks, or the like. At least some of the one or more storage compartments may include one or more safety devices (e.g., air masks, personal floatation devices, or the like).

The storage compartment 110 may include one or more shelves and/or a door. For example, the door may be fully-opaque or solid. By way of another example, the door may be at least partially fabricated from a transparent material (e.g., glass, plastic, or the like) or include a patterned or unpatterned set of cut-outs configured or designed to meet aviation guidelines and/or standards.

In some embodiments, the one or more passenger compartments 102 includes a footwell 112. For example, the footwell 112 may be defined within an open area in the passenger compartment 102. By way of another example, the footwell 112 may be defined within the divider wall 104 (e.g., defined within a divider wall element of the divider wall 104). By way of another example, the footwell 112 may be defined within or under an auxiliary monument 108. The passenger compartment 102 may be configured with the footwell 112 positioned proximate to the opening of the passenger compartment 102, such that a passenger or crew member may walk past the footwell 112 prior to reaching the aircraft seat 106. It is noted herein, however, the passenger compartment 102 may be configured such that the opening of the passenger compartment 102 is positioned between the footwell 112 and the aircraft seat 106, or proximate to the aircraft seat 106

In some embodiments, the one or more passenger compartments 102 includes an ottoman 114. The ottoman 114 may be positioned within the footwell 112. The ottoman 114 may be usable by a passenger in the aircraft seat 106 when the corresponding aircraft seat 106 is in the upright or raised position, the one or more reclined or lounge positions, and/or the lie-flat or bed position. For example, the ottoman 114 may form a portion of a bed surface when the corresponding aircraft seat 106 is in the lie-flat or bed position. The ottoman 114 may be usable by a passenger in an aircraft seat 106 positioned proximate to the passenger compartment 102 when the corresponding aircraft seat 106 is in a reclined or lounge position.

The ottoman 114 may be configured to translate and/or rotate about an axis through a sidewall of the ottoman 114 to direct a top surface to a passenger occupying the aircraft seat 106. For example, where the ottoman 114 may be configured to both translate and rotate, the ottoman 114 may be configured to independently rotate and/or translate. By way of another example, where the ottoman 114 may be configured to both translate and rotate, a rotation may prevent further translation until the ottoman 114 is returned to a select position and/or a translation may prevent further rotation until the ottoman 114 is returned to a select position.

One or more dimensions of the footwell 112 may be changed by transitioning the aircraft seat 106 between the upright or raised position, the one or more lounge or reclined positions, and the lie-flat or bed position. It is noted herein that a portion of the ottoman 114 may be actuatable (e.g., along a set of tracks or linear rails) to a position outside of the footwell 112.

It is noted herein, however, the aircraft seat 106 and/or the ottoman 114 may be limited to an upright or raised position and/or one or more lounge or reclined positions. In addition, it is noted herein the aircraft seat 106 may be the sole component forming a bed when the aircraft seat 106 is in a lie-flat or bed position. Therefore, the above description should not be interpreted as a limitation on the present disclosure but merely an illustration.

In some embodiments, the passenger compartment 102 includes one or more accessories coupled to the aircraft seat 106.

The one or more accessories may include one or more electronics or electronic devices. For example, the one or more electronics or electronic devices may include, but are not limited to, in-flight entertainment (IFE) devices 116 attached to a vertical (or substantially vertical) surface, one or more speakers configured to provide media content separate from the media content shown on the one or more IFE devices 116 and/or accompanying the media content shown on the one or more IFE devices 116, or the like. For instance, the surface may be formed by the positioning of the divider wall 104 (e.g., the forward surface, the rearward surface, or the like). It is noted herein, however, the one or more IFE devices 116 may be coupled to other monuments (e.g., in an actuatable position or a fixed position) within the aircraft cabin 100. In addition, it is noted herein, the one or more IFE devices 116 may be fixed in position or may be movable from a stowed position to one or more viewing positions via actuation in one or more translational directions and/or one or more rotational directions.

The one or more accessories may include one or more installed passenger amenities. For example, the one or more installed passenger amenities may include one or more lights and/or one or more control devices 118. For instance, the one or more control devices 118 may include, but are not limited to, an aircraft seat 106 actuation device (e.g., controls, or the like), an air flow control device (e.g., heating, ventilation, and air-conditioning (HVAC) control device), a temperature control device, or the like. It is noted herein the one or more IFE devices 116 may operate as a media content provider and a control device 118 (e.g., a touchscreen aircraft seat 106 actuation device, a touchscreen air flow control device or temperature control device, or the like).

The one or more control devices 118 may be coupled to and/or partially inset within the one or more suite wall elements of the divider wall 104 or other locations within the passenger compartment 102. The one or more control devices 118 may be coupled to and/or partially inset within an aircraft seat 106. The one or more control devices 118 may be in a housing separately integrated within or coupled to the aircraft seat 106. The one or more control devices 118 may be in a common housing integrated within or coupled to the aircraft seat 106.

In some embodiments, cabin air ventilation systems 122 generate combined air or cabin air 120 by mixing recirculated air 120a from within an aircraft cabin and outside or "fresh" air 120b from outside the aircraft cabin (e.g., where fresh air is compressed by an electric compressor or bled from an aircraft engine). For example, the cabin air 120 may be a 1:1 mixture of recirculated air 120a and fresh air 120b (e.g., 50 percent (%) recirculated air and 50% fresh air). However, energy savings (e.g., fuel savings) may dictate a decrease in an amount of fresh air used for conditioning, resulting in an increase in an amount of recirculated air 120a being used and thus an increase in the ratio between the recirculated air 120a and the fresh air 120b. The increase in the amount of recirculated air 120a, or recirculated air percentage, may result in a possible outperforming of the cabin air ventilation system 122 within the aircraft cabin 100, leading to a possible leakage and increase in recirculated contaminants and a subsequent lowering of air quality within the aircraft cabin 100.

The air quality level of the cabin air 120 may be controlled or otherwise affected, at least in part, by one or more components within the cabin air ventilation systems 122. For example, the cabin air ventilation systems 122 may include high energy particular air (HEPA) filters within a recirculation loop of the cabin air ventilation systems 122 (e.g., recirculation filters). By way of another example, the aircraft cabin 100 may include a high air change rate, diluting any contaminants within the cabin air 120. For instance, vents or valves uniformly distributed throughout a length and width of the aircraft cabin 100 may be designed to generate circular airflow patterns within a section of the aircraft cabin 100, so that the spread of contaminants between rows of aircraft seats 106 along the length of the aircraft cabin 100 may be reduced. It is noted herein, however, the circular airflow patterns may not prevent the dispersion of contaminants within a same row of aircraft seats 106, and/or may not prevent a dispersal of contaminants between adjacent rows of aircraft seats 106 caused by a person walking within an aircraft aisle of the aircraft cabin 100.

Additionally, air within aircraft cabins 100 is known to have extremely low relative humidity (approximately 10%). With FAA requirements of a minimum of 10 cubic feet of fresh air per minute at 8,000 feet pressure altitude and at a cabin temperature of 75 degrees Fahrenheit (° F.), it may be difficult to maintain a healthy and comfortable air quality level for passengers in the aircraft cabin 100.

Due to a perceived role of commercial airlines in the spread of viruses and other diseases around the globe, along with possible decisions made with respect to the operating of existing cabin air ventilation systems 122, there is an increase of concern for a safer and healthier aircraft environment. To promote a generation of the safer and healthier aircraft environment, airlines may desire to provide clean air solutions to passengers and crew members, where the clean air solutions replace or supplement existing cabin air ventilation systems 122.

Existing cabin air ventilation systems 122, however, may require modifications including, but not limited to, additional ducting (which comes with a corresponding increase in weight) and additional required maintenance (e.g., additional filters requiring replacement, or the like).

As such, it would be beneficial to provide a personal aircraft seat air treatment system 124. The personal aircraft seat air treatment system 124 may increase air quality for improved health and safety measures. The personal aircraft seat air treatment system 124 may supplement components in an existing cabin air ventilation system 122 and may be implemented without a considerable reconfiguration of the existing cabin air ventilation system 122, without a considerable increase in aircraft cabin installation weight, and/or without a considerable increase in required maintenance.

Cabin air 120 from the cabin air ventilation system 122 may flow into a passenger compartment 102 from the personal aircraft seat air treatment system 124 through one or more ventilation output components 126. For example, the one or more ventilation output components 126 may include one or more vents, grates, nozzles, ports, openings, or the like configured to output treated air to a passenger seated in the aircraft seat 106. For instance, the treated air may be output through a vent positioned proximate to the aircraft seat 106. In addition, the treated air may be output through an opening or nozzle in the aircraft seat 106.

FIGS. 2A-6 in general illustrate example embodiments of the personal aircraft seat air treatment system 124, in accordance with one or more embodiments of the present disclosure. It is noted herein "personal aircraft seat air treatment system" and variants of the term including, but not limited to, "air treatment system," "treatment system," "system," or the like may be considered equivalent, for purposes of the present disclosure.

It is noted herein some or all of the components of the treatment system 124 may be installed on an aircraft seat 106 within an aircraft cabin 100. In addition, it is noted herein some or all of the components of the treatment system 124 may be installed on an aircraft seat 106 and one or more additional aircraft seat 106. Further, it is noted herein some or all of the components of the treatment system 124 may be integrated within a personal HVAC system installed on the aircraft seat 106, or one or more additional aircraft seats 106, within the aircraft cabin 100.

In some embodiments, the aircraft seat air treatment system 124 includes one or more treatment components 200. The one or more treatment components 200 may be configured to treat (e.g., purify, humidify, sterilize, scrub, disinfect, sanitize, filter, de-odorize, or the like) the cabin air 120 to generate treated air 202. For example, the one or more treatment components 200 may include, but are not limited to, one or more filters or filtration systems. In general, the one or more treatment components 200 may include any number of systems, sub-systems, and/or components capable of treating the cabin air 120 received from the cabin air ventilation system 122 and/or the environment surrounding the aircraft seat 106 including the treatment system 124, and supplying the treated air 202 to a breathing area of a passenger occupying the aircraft seat 106 via the one or more ventilation output components 126. For example, the breathing area may be an area near a passenger's head when the passenger is seated in an upright or raised position, seated in one or more lounge or reclined positions, and/or resting in a lie-flat or bed position, where the one or more ventilation output components 126 are positioned within the passenger compartment 102 accordingly (e.g., as illustrated in FIGS. 1A-1D).

The air treatment system 124 may be positioned within the passenger compartment 102 for increased ease of access to replaceable (e.g., removable and/or insertable), and/or repairable components of the personal aircraft seat air treatment system 124. For example, components including, but not limited to, the one or more treatment components 200 (e.g., purifiers or filters as described through the present disclosure, or the like) may be located in accessible cavities within the passenger compartment 102 (e.g., storage compartments 110, footwell 112, or the like), and/or may be accessible through access panels installed in the passenger compartment 102 (e.g., access panels in the divider wall 104, or the like).

The air treatment system 124 may include or may be fluidically coupled to an air blower 204. For example, the air blower 204 may receive an amount of input air. For instance, the input air may be cabin air 120 generated from a mixture of recirculated air 120a and fresh air 120b. In addition, the cabin air 120 may be received from a cabin air ventilation system 122 installed within the aircraft cabin 100. It is noted herein, however, the amount of cabin air 120 may be pulled from the environment within the aircraft cabin 100 surrounding the aircraft seat 106.

The treatment system 124 may include or may be fluidically coupled to ductwork 206 through the aircraft seat 106, such that the air blower 204 may supply the cabin air 120 to the ductwork 206. One or more of the ductwork 206 or the air blower 204 may be fluidically coupled to the one or more treatment components 200, such that one or more of the ductwork 206 or the air blower 204 may supply the cabin air 120 to the one or more treatment components 200.

In some embodiments, the air treatment system 124 includes a control device 118. For example, the control device 118 may be an HVAC control module 118. The control device 118 may be communicatively coupled to at least some of the one or more treatment components 200. For example, the control device 118 may be configured to adjust the operation of the one or more treatment components 200. The control device 118 may be communicatively coupled to at least some of the one or more ventilation output components 126 for air distribution. For example, the control device 118 may be configured to adjust the operation of the one or more ventilation output components 126.

In some embodiments, the air treatment system 124 includes one or more sensors 208 coupled to the control device 118. For example, the one or more sensors 208 may be configured to monitor (e.g., sense a change in) rate of airflow through the air treatment system 124, and/or the air quality (e.g., temperature, humidity, level of contamination, or the like) in the cabin air 120 passing through the air treatment system 124, and the control device 118 may be configured to adjust the components of the air treatment system 124 in response. By way of another example, the one or more sensors 208 may be configured to monitor (e.g., sense a change in) air quality (e.g., temperature, humidity, level of contamination, or the like) in the environment surrounding the aircraft seat 106, and the control device 118 may be configured to adjust the components of the air treatment system 124 in response.

FIGS. 2A-2E illustrate an example embodiment of the air treatment system 124, in accordance with one or more embodiments of the present disclosure.

In some embodiments, the one or more treatment components 200 may include, but are not limited to, one or more purifiers 210. For example, the one or more purifiers 210 may include, but are not limited to, ultraviolet (UV) germicidal irradiation lamps (or UV lamps). For instance, the UV lamps may treat the input air via UV light emitted to purify the air and generate purified air. The UV lamps may be in a constant on state, in a timed of switched on/off state, or may be controlled via the control device 118 in response to information received from the one or more sensors 208. It is noted herein that where all the cabin air 120 is passed through the one or more purifiers 210, the resultant purified air is also the treated air 202.

In one non-limiting example, the one or more purifiers 210 may be positioned along ductwork 206 leading to the aircraft seat 106 via an aircraft seat headrest nozzle (e.g., a ventilation output component 126). In this example, the aircraft seat headrest nozzle 126 may be configured to output the treated air 202, such that only the select ventilation output components 126 may be considered components of the air treatment system 124, while other ventilation output components 126 (e.g., including, but not limited to, the aircraft seat pan or seat base nozzle, the aircraft seat lower back nozzle, and the aircraft seat upper back nozzle) may be configured to output cabin air 120 (e.g., non-treated air).

In another non-limiting example, the one or more purifiers 210 may be positioned along ductwork 206 leading to all of the one or more ventilation output components 126 (e.g., to the aircraft seat pan or seat base nozzle, the aircraft seat lower back nozzle, the aircraft seat upper back nozzle, and/or the aircraft seat headrest nozzle). It is noted herein the one or more purifiers 210 may be located such that a central purifier 210 is used for some or all of the ventilation output components 126 (e.g., prior to ductwork 206 leading to the ventilation output components 126). In addition, it is noted herein the one or more purifiers 210 may be located such that each ventilation output component 126 has a corresponding purifier 210.

In another non-limiting example, the one or more purifiers 210 may be positioned in the air blower 204, effectively acting as a central purifier 210 for all ventilation output components 126.

The cabin air 120 passing through the ductwork 206 and the subsequent treated air 202 passing through the one or more treatment components 200 prior to being outputted by the one or more ventilation output components 126 may include a laminar flow with low air velocities. For example, the laminar flow may ensure an adequate amount of time is achieved when exposing the cabin air 120 to the UV light from the UV lamps. The laminar flow may ensure a desired level of treating of the cabin air 120. The laminar flow may provide a comfortable airflow rate of the treated air around the face of a passenger occupying the aircraft seat 106.

Although embodiments of the present disclosure illustrate the cabin air 120 passing through the one or more purifiers 210, it is noted herein the cabin air 120 may be separated into a first portion of cabin air 120 and a second portion of cabin air 120 prior to the one or more purifiers 210. Here, the first portion of cabin air 120 may pass through the one or more purifiers 210 to generate purified air, while the second portion of cabin air 120 is routed via ductwork 206 to mix with the purified air after the one or more purifiers 210 to generate the treated air 202.

Figure 3:
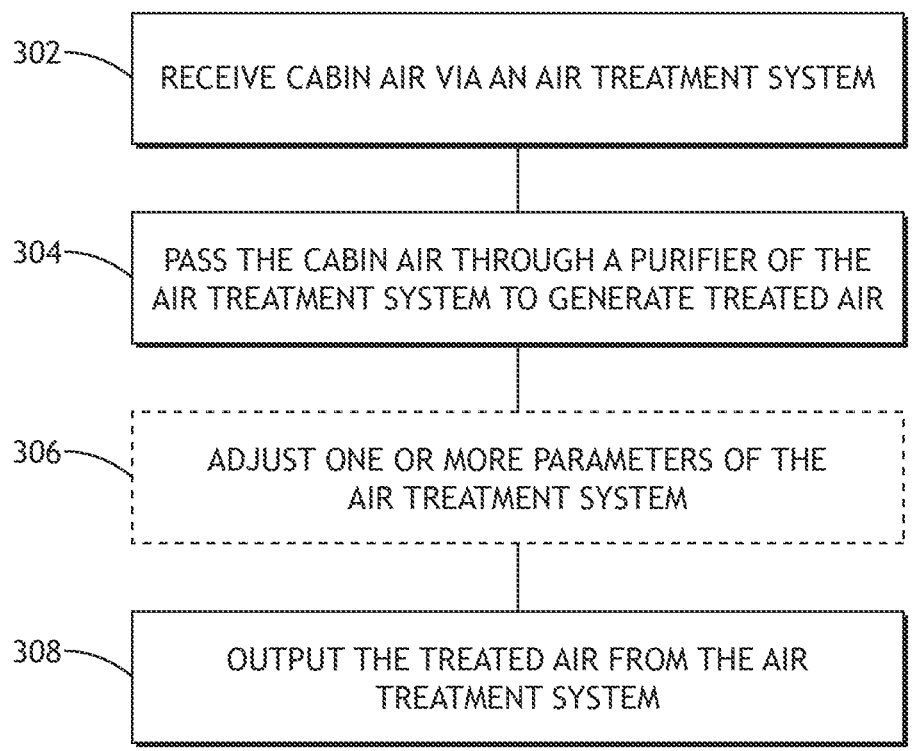
FIG. 3 is a flow diagram illustrating steps performed in a method or process for treating air, according to one or more embodiments of the present disclosure.
Figure 4A:
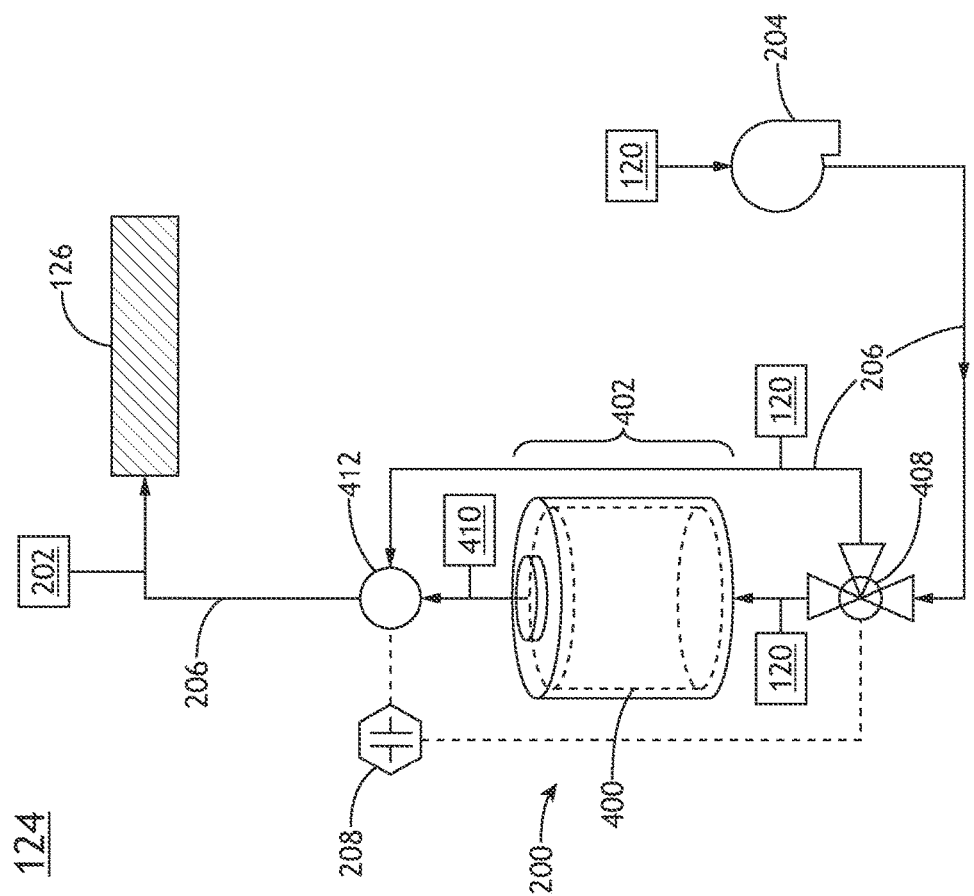
FIG. 4A is a block diagram schematic illustrating a personal aircraft seat air treatment system, according to one or more embodiments of the present disclosure.
Figure 4B:
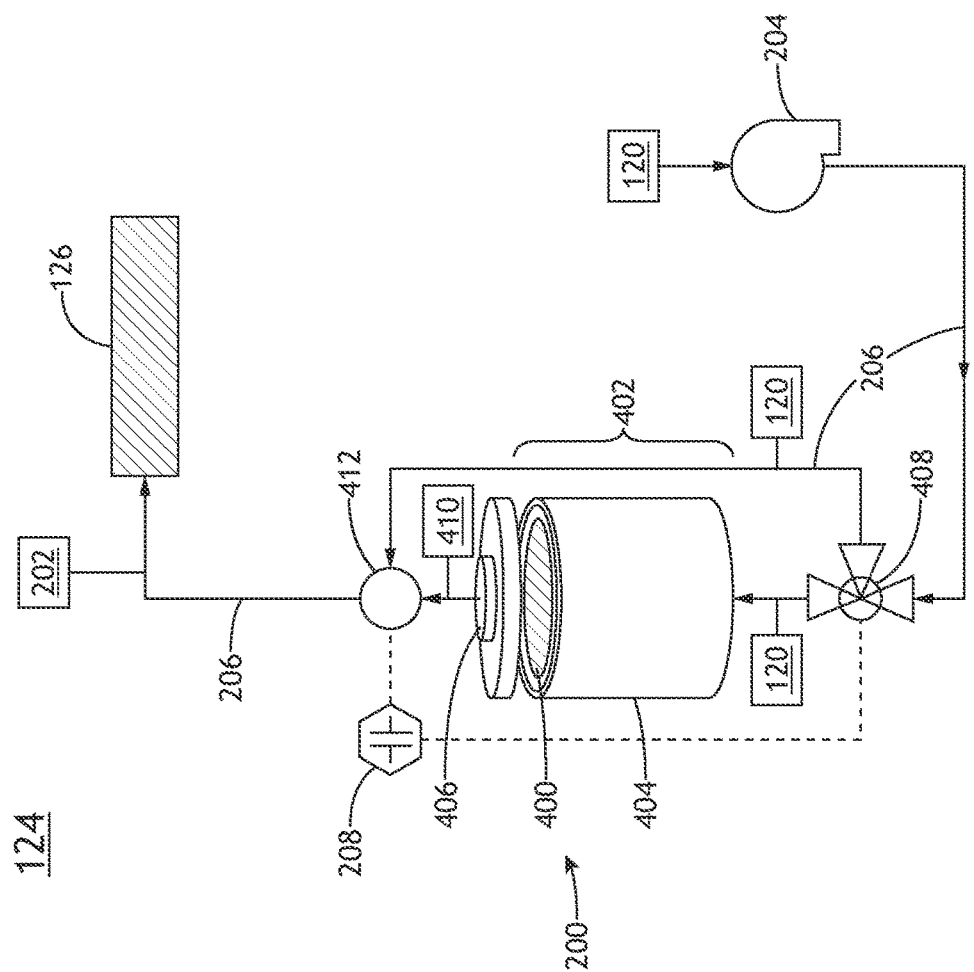
FIG. 4B is a block diagram schematic illustrating a personal aircraft seat air treatment system, according to one or more embodiments of the present disclosure.
Figure 4C:
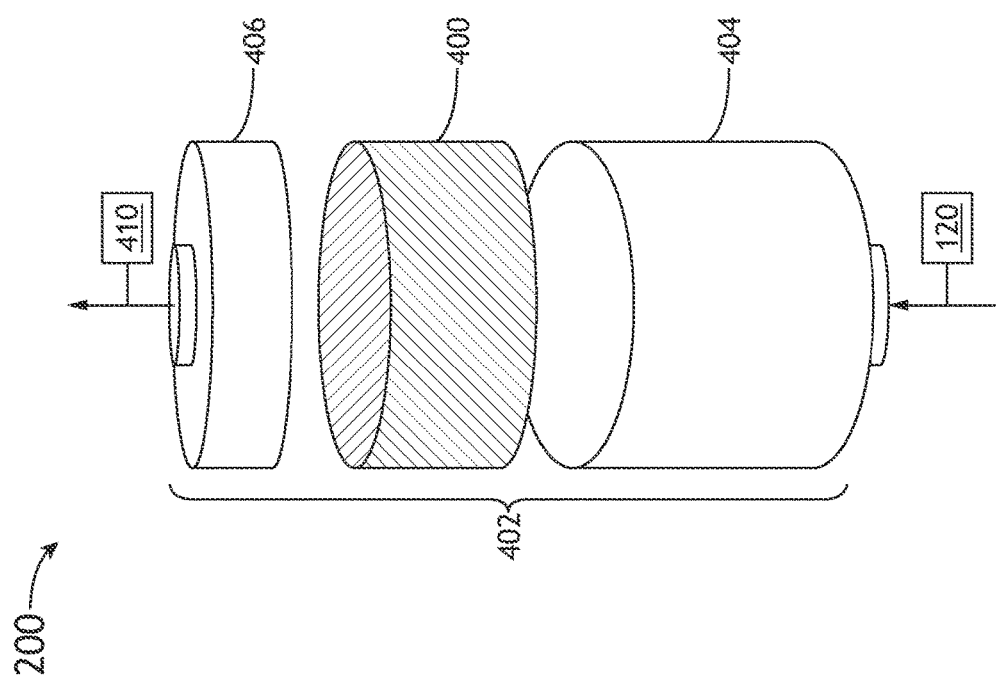
FIG. 4C is an exploded block diagram schematic illustrating a portion of a personal aircraft seat air treatment system, according to one or more embodiments of the present disclosure.
Figure 4D:
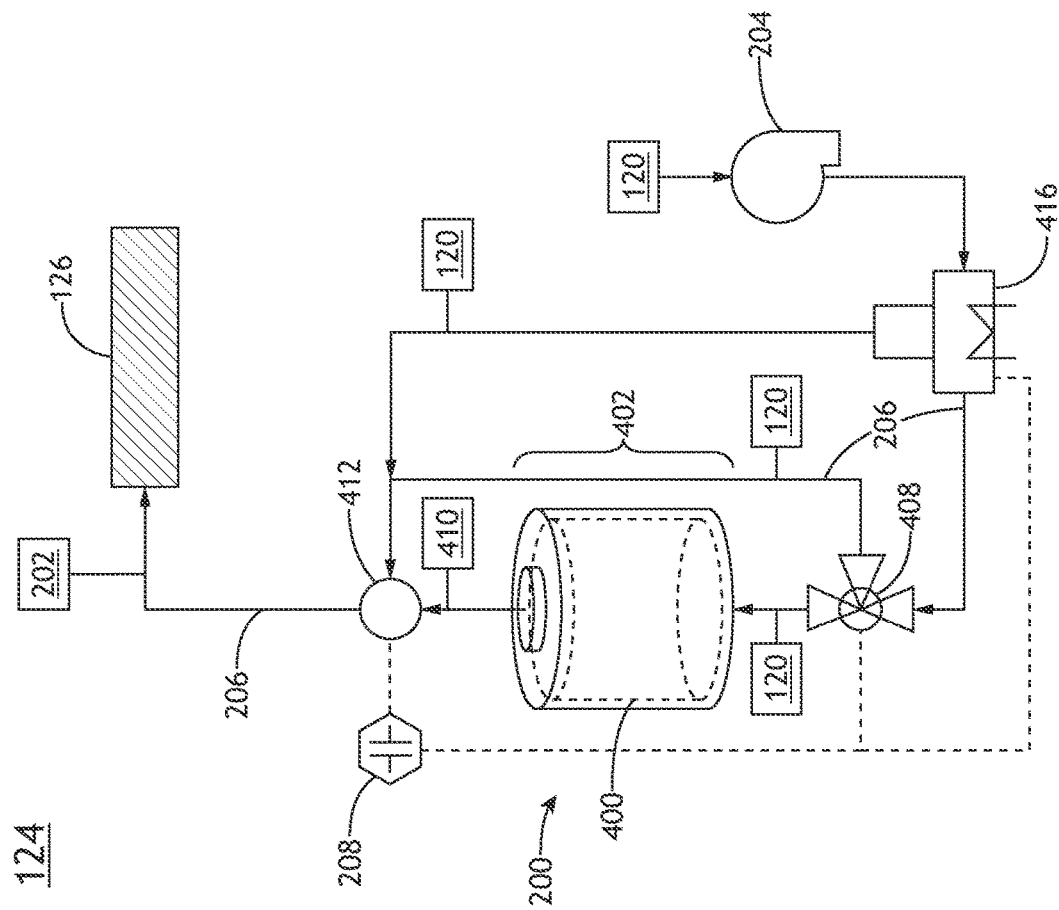
FIG. 4D is a block diagram schematic illustrating a personal aircraft seat air treatment system, according to one or more embodiments of the present disclosure.
Figure 4E:
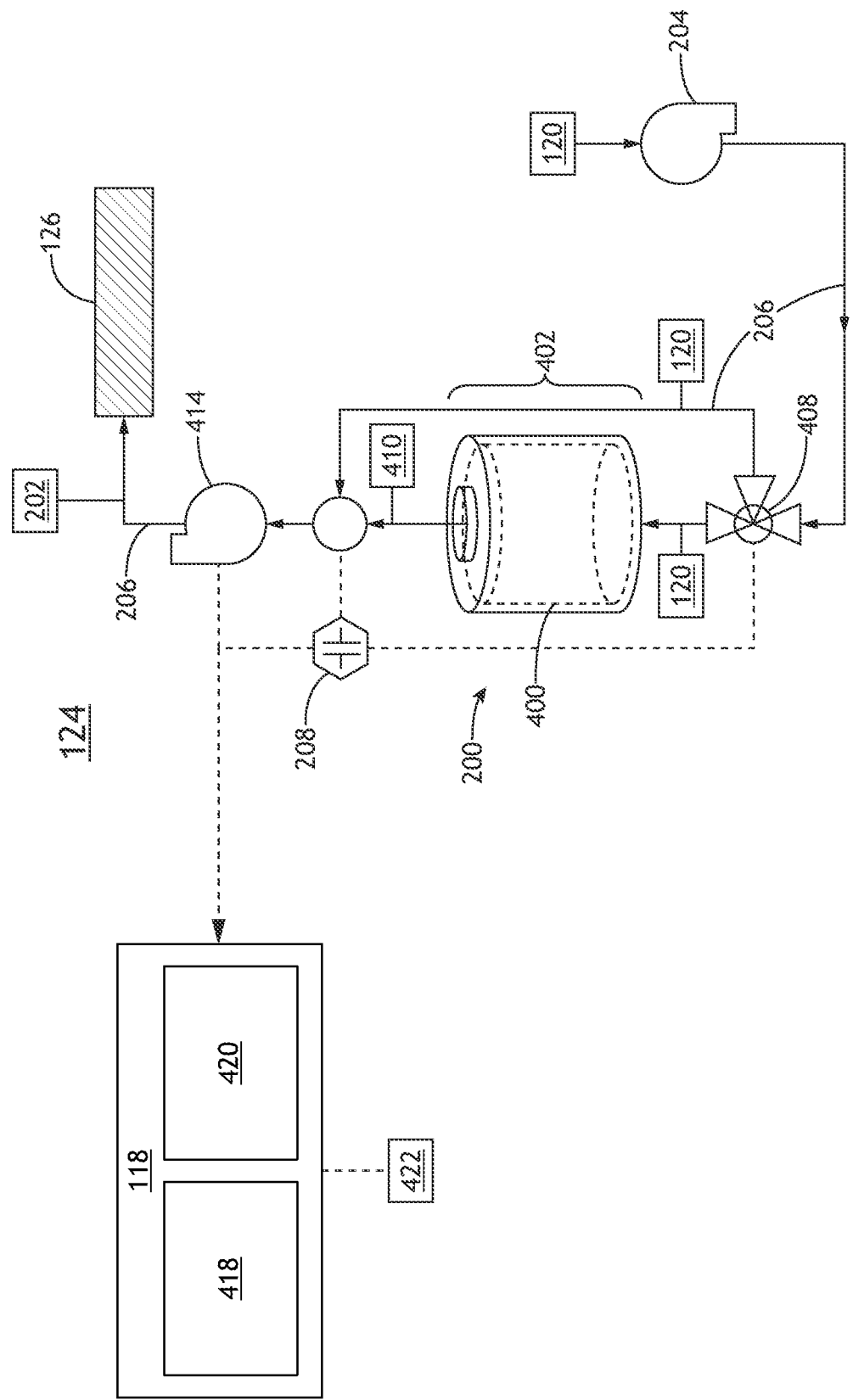
FIG. 4E is a block diagram schematic illustrating a personal aircraft seat air treatment system, according to one or more embodiments of the present disclosure.

FIG. 3 is a flow diagram of a method or process 300 for treating air with the air treatment system 124, in accordance with one or more embodiments of the present disclosure. It is noted herein that the steps of the method or process 300 may be implemented all or in part by the air treatment system 124 as illustrated in at least FIGS. 2A-2E. It is further recognized, however, that the method or process 300 is not limited to the air treatment system 124 as illustrated in at least FIGS. 2A-2E in that additional or alternative system-level embodiments may carry out all or part of the steps of method or process 300.

In a step 302, cabin air 120 is received via the air treatment system 124. In some embodiments, the cabin air 120 is received from a cabin air ventilation system 122 within the aircraft cabin 100. The cabin air 120 may flow through the air blower 204. For example, the cabin air may flow through ductwork 206 between the air blower 204.

In a step 304, the cabin air 120 is passed through a purifier 210 of the air treatment system 124 to generate treated air 202. In some embodiments, the purifier 210 may include, but is not limited to, a UV lamp. The cabin air 120 may be exposed to the UV lamps, the emitted UV light from which may purify a portion of the cabin air 120 to generate the treated air 202.

In a step 306, one or more parameters of the air treatment system 124 are adjusted. In some embodiments, where the surrounding environment or air within the air treatment system 124 is determined to be outside of user-selected or pre-set levels, one or more parameters of components of the air treatment system 124 as described throughout the disclosure may be adjusted. For example, the parameters may be adjusted to offset the surrounding environment. By way of another example, the parameters may be adjusted to correct air flow within the air treatment system 124. It is noted herein, however, that where the user-selected or pre-set levels are correct, no adjustment may be required for the air treatment system 124. In this regard, step 306 may be optional.

In a step 308, the treated air 202 is outputted from the air treatment system 124. In some embodiments, the treated air 202 is outputted via the one or more ventilation output components 126.

FIGS. 4A-4E illustrate example embodiments of the air treatment system 124, in accordance with one or more embodiments of the present disclosure.

In some embodiments, the one or more treatment components 200 may include, but are not limited to, a hydrogel cartridge 400. For example, the hydrogel cartridge 400 may be a super-hygroscopic hydrogel configured to absorb water at multiple times their weight & release under partial pressure differential conditions (e.g., in the absence of heat). The hydrogel cartridge 400 may include any hydrogel structure. For example, the hydrogel structure may include, but is not limited to, beads, a wick, a sheet, a layered sheet, a tube, a capsule, or the like. The hydrogel cartridge 400 may include any antibacterial or antimicrobial mechanism known in the art to maintain cleanliness and mitigate bacterial and/or microbial growth in and on the hydrogel cartridge 400. For example, the mechanism may include, but is not limited to, an additive and/or a hermetically sealed bag. The hydrogel cartridge 400 may be replaced at set intervals (e.g., based on hours of use, after every aircraft flight, or the like) to ensure cleanliness.

In some embodiments, the air treatment system 124 includes or is fluidically coupled to a cannister 402. The cannister 402 may include a main body or bottom 404 and a cannister lid 406. The hydrogel cartridge 400 is replaceable (e.g., removable and/or insertable) when the cannister lid 406 is disengaged. For example, the hydrogel cartridge 400 may be replaced with another hydrogel cartridge 400 by releasing the hydrogel cartridge 400 from the cannister 402 and removing the cannister lid 406 from the main body or bottom 404. It is noted herein the cannister lid 406 may be coupled to (or engage) the main body or bottom 404 via friction or an interference fit, via any interlocking assembly known in the art, via fasteners, or the like. It is noted herein, however, the cannister 402 may be a sealed unit with the hydrogel cartridge 400 sealed inside, such that the cannister 402 is replaced in its entirety when the hydrogel cartridge 400 is replaced.

Although the cannister 402 is illustrated as a cylinder in FIGS. 4A-4E, it is noted herein the cylindrical volume should not be considered limiting. For example, the cannister 402 may be a cube. Therefore, the above description should not be interpreted as a limitation on the present disclosure but merely an illustration.

In some embodiments, the air treatment system 124 includes an air input valve 408. The air input valve 408 may be fluidically coupled to the air blower 204 via ductwork 206, which may supply the cannister 402 with an amount of input air (e.g., cabin air 120). The air input valve 408 may draw in a first portion of the cabin air 120 into the cannister 402 of the air treatment system 124. The air input valve 408 may separate a second portion of the cabin air 120 into a second set of ductwork 206, which may be re-added into humidified air 410 after the cannister 402 by an air mixer 412 fluidically coupled to the cannister 402 to generate treated air 202, as illustrated by at least FIG. 4A.

The hydrogel cartridge 400 may treat at least a portion of the cabin air 120. For example, the first portion of cabin air 120 would flow through the cannister 402 and the hydrogel cartridge 400 to become humidified air 410, the second portion of cabin air 120 would flow directly from the air input valve 408 to the air mixer 412 to combine with the humidified air 410 to become treated air 202.

Figure 5A:
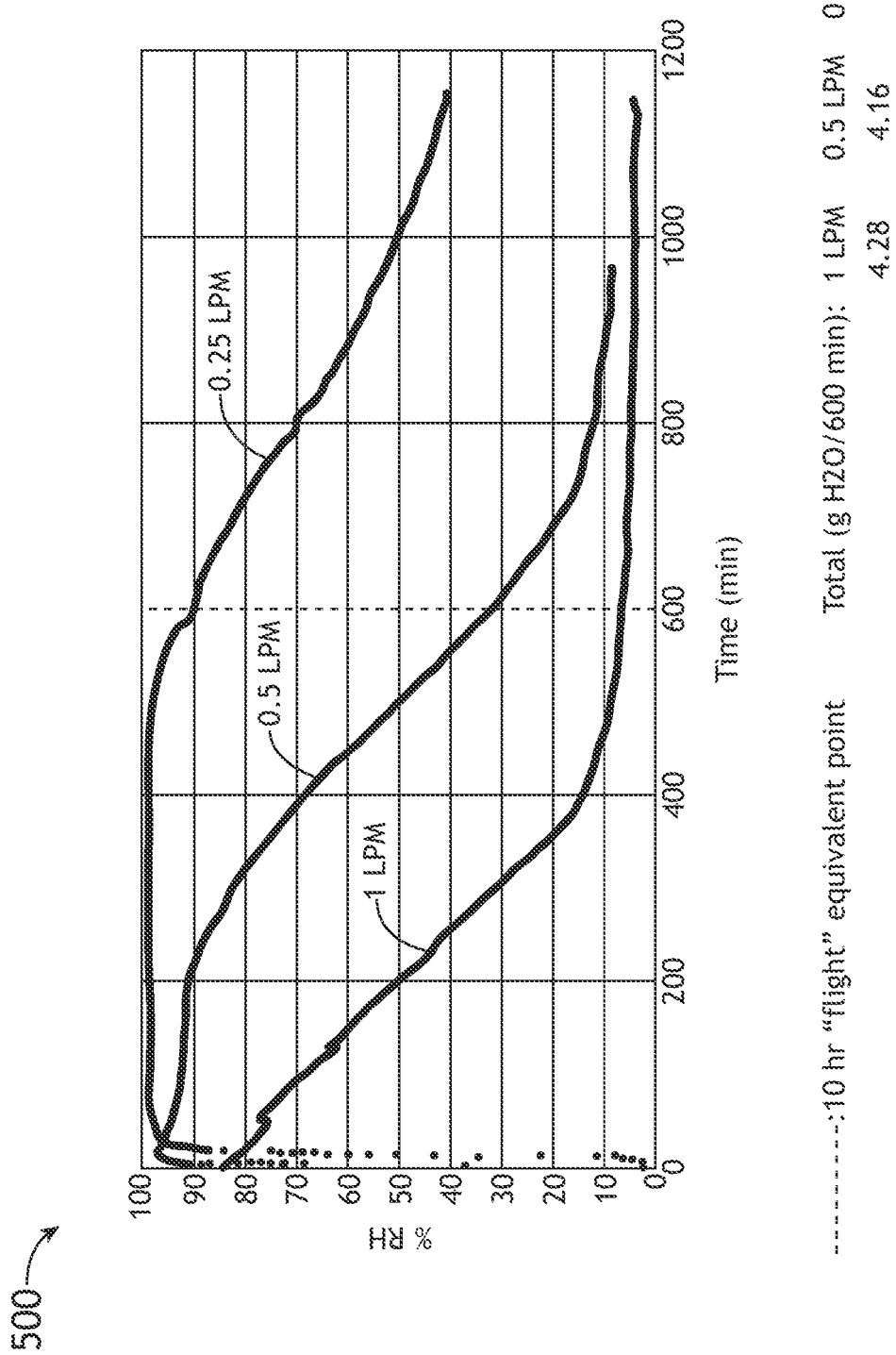
FIG. 5A illustrates a graph comparing percent relative humidity over time, according to one or more embodiments of the present disclosure.

As illustrated in graph 500 in FIG. 5A, the hydrogel cartridge 400, when subjected to an air flow, is able to hydrate the air in relatively minimal time for extended periods. For example, 5 grams hydrogel, taking 10-20 seconds for water absorption to achieve 90% water/hydrogel weight, may afford up to 1 liter per minute (LPM) of ambient-temperature (T) cabin air flow hydration measured in percent relative humidity (% RH), measured in grams of water per minute (g H2O/min). It is noted herein that FIG. 5A illustrates % RH over time for 1 LPM air flow, 0.5 LPM air flow, and 0.25 LPM air flow. Based on FIG. 5A, it is projected that approximately 1 pound of hydrogel and 1 pound of water (0.45 kilograms of hydrogel and water) can humidify about 100 liters per minute of cabin air without recirculation.

It is herein noted that the cannister 402 may be approximately 0.5 to 5 liters in volume to house the hydrogel cartridge 400, being limited by the space available for the placement of the cannister 402 within the passenger compartment 102. In one non-limiting example, the air treatment system 124 may raise the humidity of the air surrounding the passenger from 10% to 30% for up to a 10-hour flight using one 590 ml water bottle.

Figure 5B:
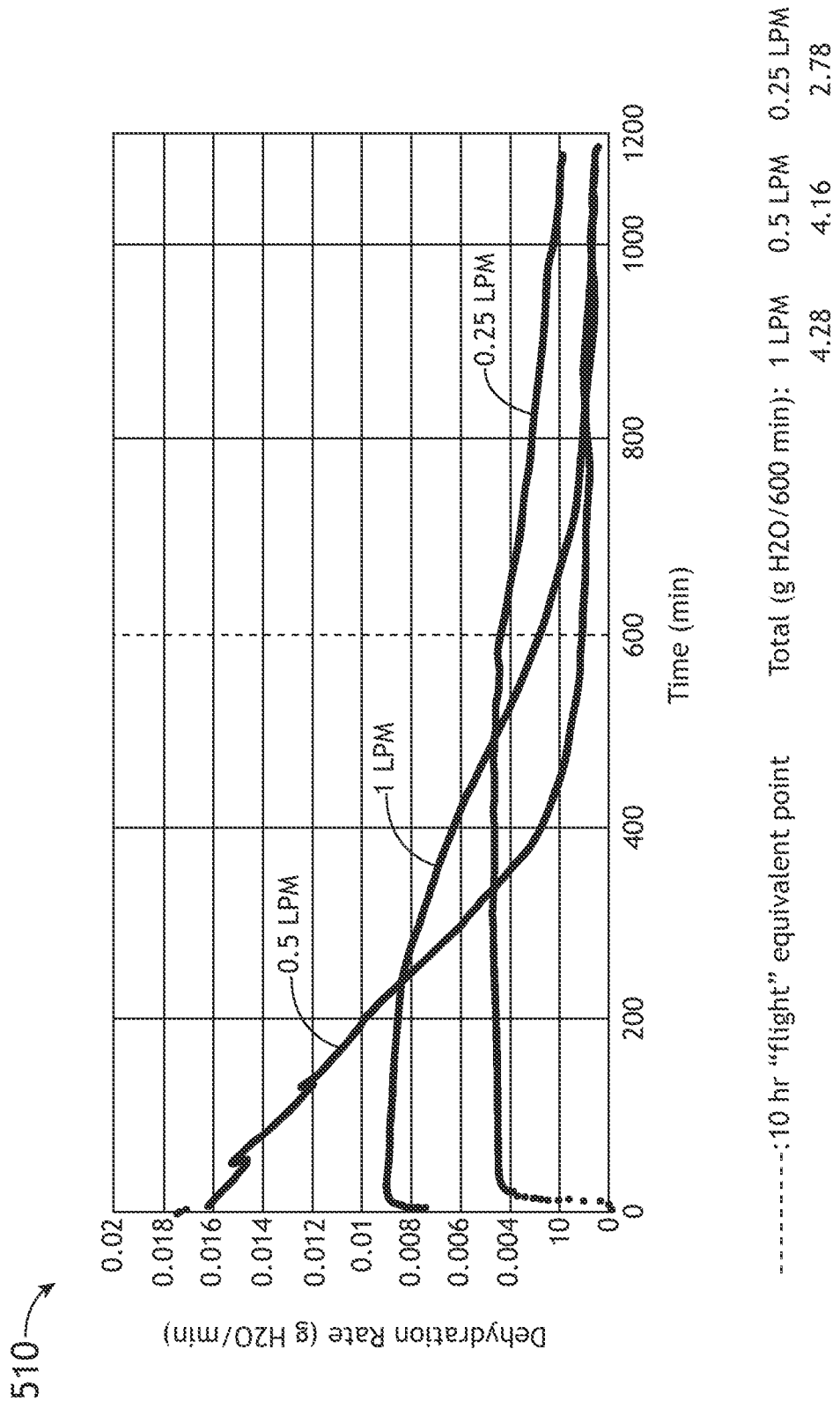
FIG. 5B illustrates a graph comparing dehydration rate over time, according to one or more embodiments of the present disclosure.

As illustrated in graph 510 in FIG. 5B, the hydrogel cartridge 400 may be dehumidified as it is used. The FAA requires approximately 7.3 cubic foot per minute of fresh air per occupant of an aircraft cabin 100, which with the typical cabin volume per occupant being about 50 cubic feet equates to 15% air volume per occupant per minute replenished with fresh air. This fresh air within the aircraft cabin 100 has approximately 10% relative humidity. For example, for a premium seat environment the volume of the passenger compartment around an occupant's head is approximately 27 cubic feet, approximately 1.25 g of water per minute is needed to hydrate the fresh air to at least 40% relative humidity with adequate margin (i.e., 20%). This water vapor input is similar to the dehydration rate of the hydrogel cartridge 400 of the present disclosure. It is noted herein that FIG. 5B illustrates dehydration rate over time for 1 LPM air flow, 0.5 LPM air flow, and 0.25 LPM air flow. It is noted herein the hydrogel cartridge 400 may be reactivated to specific water content levels after use being dehydrated.

Although embodiments of the present disclosure illustrate separating the cabin air 120 into a first portion of cabin air 120 that is treated by the hydrogel cartridge 400 to become humidified air 410 and a second portion of cabin air 120 that is mixed with the humidified air 410 via the air mixer 412 to generate the treated air 202, it is noted herein all of the cabin air 120 may be passed through the hydrogel cartridge 400 such that the air mixer 412 is not a required or necessary component. Where all of the cabin air 120 is passed through the hydrogel cartridge 400, the resultant humidified air 410 is also the treated air 202.

In some embodiments, the air treatment system 124 includes an output blower 414. The control device 118 may be configured to control the output blower 414 to increase or decrease air flow of the treated air 202 to the passenger in the aircraft seat 106.

In some embodiments, the air treatment system 124 includes one or more temperature-adjusting components 416. For example, the one or more temperature-adjusting components 416 may increase or decrease the temperature of the amount of input air (e.g., the cabin air 120) and/or the treated air 202, depending on the location of the temperature-adjusting components 416 within the air treatment system 124. For example, the temperature adjustment may be in response to a received passenger input. By way of another example, the temperature adjustment may be a pre-determined adjustment following a sensed change via one or more sensors 208 in the air treatment system 124, in the environment surrounding the aircraft seat 106, in the aircraft seat 106 (e.g., due to passenger body heat), or the like.

It is noted herein the air blower 204, the ductwork 206, the one or more treatment components 200, the one or more ventilation output components 126, the cannister 402, or other components of the air treatment system 124 may include one or more valves. For example, the one or more valves may include, but are not limited to, one-way valves. For instance, the one or more valves may be configured to prevent backflow into the cabin air ventilation system 122.

In this regard, the treated air 202 may pass through the one or more ventilation output components 126 to a passenger in the aircraft seat 106. For example, ductwork 206 may fluidically couple the air mixer 412 to the one or more ventilation output components 126 and the ductwork 206, and the treated air 202 may pass through the ductwork 206 to the one or more ventilation output components 126.

The control device 118 may include or be communicatively coupled to one or more components of the air treatment system 124. For example, the control device 118 may control the air mixer 412, which may in turn adjust the ratio of treated air/input air from the air mixer 412 based on the measurements from the one or more sensors 208.

The control device 118 may control one or more components of the air treatment system 124 following a received passenger input. The control device 118 may control one or more components of the air treatment system 124 by performing a pre-determined adjustment following a sensed change via one or more sensors 208 in the air treatment system 124, in the environment surrounding the aircraft seat 106, in the aircraft seat 106 (e.g., due to passenger body heat), or the like.

The control device 118 may include one or more processors 418 and memory 420, where the memory 420 is configured to store a set of program instructions, where the one or more processors 418 are configured to execute program instructions causing the one or more processors 418 to perform one or more steps of the methods or processes as described throughout the disclosure. For example, the control device 118 may be configured to adjust one or more parameters of the personal aircraft seat air treatment system 124.

The one or more processors 418 may include any processor or processing element known in the art. For the purposes of the present disclosure, the term "processor" or "processing element" may be broadly defined to encompass any device having one or more processing or logic elements (e.g., one or more graphics processing units (GPU), microprocessing units (MPU), systems-on-a-chip (SoC), one or more application specific integrated circuit (ASIC) devices, one or more field programmable gate arrays (FPGAs), or one or more digital signal processors (DSPs)). In this sense, the one or more processors 418 may include any device configured to execute algorithms and/or instructions (e.g., program instructions stored in memory). In one embodiment, the one or more processors 418 may be embodied as a desktop computer, mainframe computer system, workstation, image computer, parallel processor, networked computer, or any other computer system configured to execute a program configured to operate or operate in conjunction with components of the air treatment system 124 and/or other components installed in the passenger compartment 102, as described throughout the present disclosure.

The memory 420 may include any storage medium known in the art suitable for storing program instructions executable by the associated respective one or more processors 418. For example, the memory 420 may include a non-transitory memory medium. By way of another example, the memory 420 may include, but is not limited to, a read-only memory (ROM), a random-access memory (RAM), a magnetic or optical memory device (e.g., disk), a magnetic tape, a solid-state drive and the like. It is further noted that the memory 420 may be housed in a common controller housing with the one or more processors 418. In one embodiment, the memory 420 may be located remotely with respect to the physical location of the respective one or more processors 418. For instance, the respective one or more processors 418 may access a remote memory (e.g., server), accessible through a network (e.g., internet, intranet, and the like).

The control device 118 may include or be coupled (e.g., physically coupled, electrically coupled, communicatively coupled, or the like) to one or more user interfaces 422. For example, the one or more user interfaces 422 may provide user inputs to the control device 118 and/or provide information to a passenger in the aircraft seat 106. For instance, the user inputs may direct the control device 118 to control select components of the air treatment system 124 and/or other components installed in the passenger compartment 102, as listed throughout the present disclosure.

The user interface 422 may include, but is not limited to, one or more desktops, laptops, tablets, and the like. The user interface 422 may include a display used to display data of the air treatment system 124 and/or other components installed in the passenger compartment 102 to a user. The display of the user interface 422 may include any display known in the art. For example, the display may include, but is not limited to, a liquid crystal display (LCD), an organic light-emitting diode (OLED) based display, or a CRT display. Those skilled in the art should recognize that any display device capable of integration with a user interface 422 is suitable for implementation in the present disclosure. In another embodiment, a user may input selections and/or instructions responsive to data displayed to the user via a user input device of the user interface 422.

The one or more user interfaces 422 may be components of the aircraft seat 106. For example, the one or more user interfaces 422 may be an aircraft accessory. It is noted herein, however, the one or more user interfaces 422 may be in the possession of a passenger (e.g., a tablet, smartphone, or other user-held personal electronic device) and configured to interface with the control device 118 via wired or wireless communication. In general, the one or more user interfaces 422 may include any type of human-machine interface.

It is noted herein the control device 118 and other components of the personal heating, ventilation, and air-conditioning (HVAC) system installed on the aircraft seat 106 within the aircraft cabin 100 in which some or all of the treatment system 124 may be integrated is further described in United Kingdom Patent Application No. 2005138.9, filed on Apr. 7, 2020, incorporated herein in the entirety.

Figure 6:
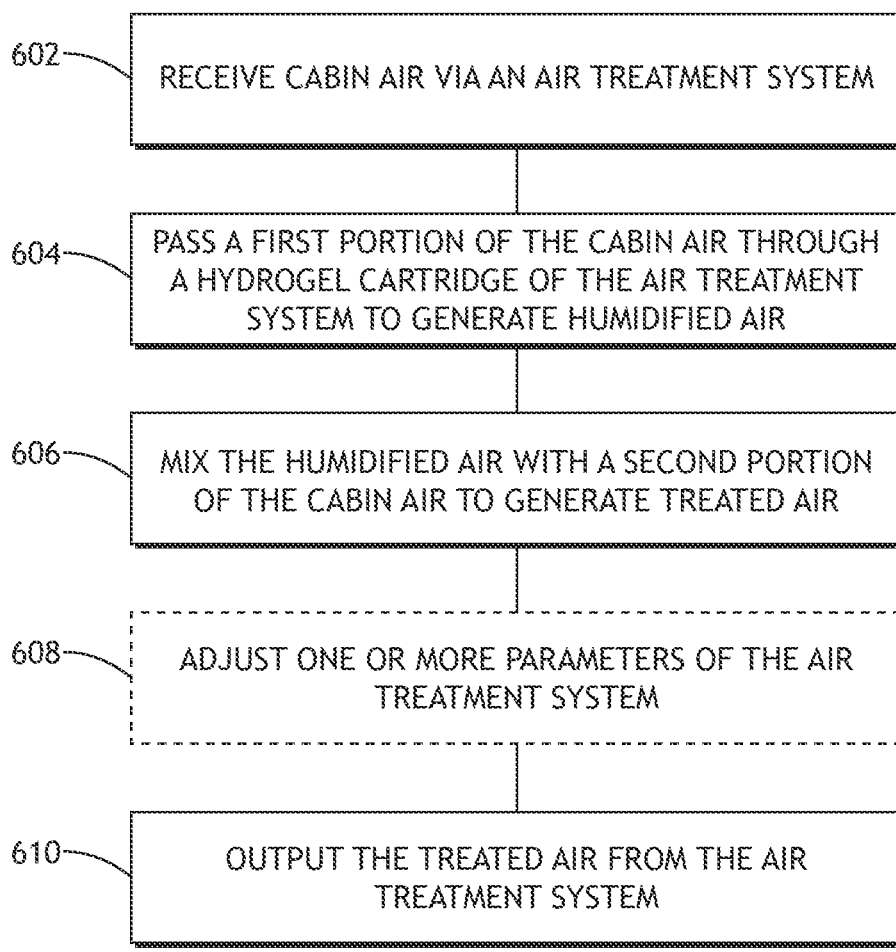
FIG. 6 is a flow diagram illustrating steps performed in a method or process for treating air, according to one or more embodiments of the present disclosure.

FIG. 6 is a flow diagram of a method or process 600 of the treating air with the air treatment system 124 in accordance with one or more embodiments of the present disclosure. It is noted herein that the steps of the method or process 600 may be implemented all or in part by the air treatment system 124 as illustrated in at least FIGS. 4A-4E. It is further recognized, however, that the method or process 600 is not limited to the air treatment system 124 as illustrated in at least FIGS. 4A-4E in that additional or alternative system-level embodiments may carry out all or part of the steps of method or process 600.

In a step 602, cabin air 120 is received via the air treatment system 124. In some embodiments, the cabin air 120 is received from a cabin air ventilation system 122 within the aircraft cabin 100. The cabin air 120 may flow through the air blower 204, which may be fluidically coupled to the air input valve 408. For example, the cabin air may flow through ductwork 206 between the air blower 204 and the air input valve 408.

In a step 604, a first portion of cabin air is passed through a hydrogel cartridge 400 of the air treatment system 124 to generate humidified air 410. In one non-limiting example, the cabin air 120 may flow into the cannister 402 via the air input valve 408, which may be connected to the cannister 402 via a coupling mechanism. A portion of the cabin air 120 may then interact with the hydrogel cartridge 400, which hydrates a portion of cabin air 120 to create humidified air 410.

In a step 606, the humidified air 410 is mixed with a second portion of the cabin air 120 to generate treated air 202. For example, treated air 202 may be combined with cabin air 120 by the air mixer 412.

In a step 608, one or more parameters of the air treatment system 124 are adjusted. In some embodiments, where the surrounding environment or air within the air treatment system 124 is determined to be outside of user-selected or pre-set levels, one or more parameters of components of the air treatment system 124 as described throughout the disclosure may be adjusted. For example, the parameters may be adjusted to offset the surrounding environment. By way of another example, the parameters may be adjusted to correct air flow within the air treatment system 124. It is noted herein, however, that where the user-selected or pre-set levels are correct, no adjustment may be required for the air treatment system 124. In this regard, step 608 may be optional.

In a step 610, the treated air 202 is outputted from the air treatment system 124. In some embodiments, the treated air 202 is outputted via the one or more ventilation output components 126.

It is noted herein any methods or processes 300, 600 listed are not limited to the steps and/or sub-steps provided. For example, the methods or processes 300, 600 may include more or fewer steps and/or sub-steps. In addition, the methods or processes 300, 600 may perform the steps and/or sub-steps simultaneously. Further, the methods or processes 300, 600 may perform the steps and/or sub-steps sequentially, including in the order provided or an order other than provided. Therefore, the above description should not be interpreted as a limitation on the scope of the present disclosure but merely an illustration.

In some embodiments, the air treatment system 124 may include one or more spargers (e.g., membrane-based, fluid-based, or the like) or other indirect-contact components (e.g., as opposed to the hydrogel, which has direct contact between the hydrogel and water), where the cabin air 120 is passed through the spargers to generate the treated air 202.

It is noted herein one or more of the embodiments directed to the air treatment system 124 as described throughout the present disclosure may be workable with the one or more spargers.

It is noted herein one or more of the embodiments directed to the air treatment system 124 may be combinable and/or interchangeable. For example, the air treatment system 124 may include aspects or components of the one or more purifiers 210, aspects or components of the one or more hydrogel cartridges 400 with cannister 402, or a combination of aspects or components of the one or more purifiers 210 and aspects or components of the one or more hydrogel cartridges 400 with cannister 402, as described throughout the present disclosure.

In addition, it is noted herein treating the cabin air 120 and then outputting the treated air 202 into a breathing area of a passenger (e.g., passenger compartment 102) occupying the aircraft seat 106 may allow for energy savings (e.g., fuel savings) by reducing bleed airflow from the engines (e.g., fresh air for a bleed system). Although reducing bleed airflow may increase the amount of recirculated air 120a, which may increase the stress on HEPA filters within the cabin air ventilation system 122, the concerns of increased level of contamination being provided to the passenger occupying the aircraft seat 106 is reduced due to the treatment system 124. In addition, it is noted herein treating the cabin air 120 and then outputting the treated air 202 into the breathing area of the passenger (e.g., passenger compartment 102) occupying the aircraft seat 106 may reduce or prevent in-row contamination and/or contamination caused by a person passing the row of aircraft seats 106 when walking in the aircraft aisle of the aircraft cabin 100.

In this regard, the personal aircraft seat air treatment system 124 may increase air quality for improved health and safety measures by sanitizing the cabin air 120 received from the existing cabin air ventilation system 122. The personal aircraft seat air treatment system 124 supplements components in the existing cabin air ventilation system 122 by receiving the cabin air 120 and is implemented without a considerable reconfiguration of the existing cabin air ventilation system 122, without a considerable increase in aircraft cabin installation weight, and without a considerable increase in required maintenance.

Components of the personal aircraft seat air treatment system 124 including, but not limited to, the one or more treatment components 200 installed within the aircraft cabin 100 may need to be configured in accordance with aviation guidelines and/or standards put forth by, but not limited to, the Federal Aviation Administration (FAA), the European Aviation Safety Agency (EASA) or any other flight certification agency or organization; the American National Standards Institute (ANSI), Aeronautical Radio, Incorporated (ARINC), or any other standards setting organization or company; the Radio Technical Commission for Aeronautics (RTCA) or any other guidelines agency or organization; or the like.

Although embodiments of the present disclosure are directed to an aviation environment, it is noted herein the personal aircraft seat air treatment system 124 and/or components of the personal aircraft seat air treatment system 124 including, but not limited to, the one or more treatment components 200 are not limited to the aviation environment and/or the aircraft components within the aviation environment. For example, the personal aircraft seat air treatment system 124 and/or components of the personal aircraft seat air treatment system 124 including, but not limited to, the one or more treatment components 200 may be configured to operate in any type of vehicle known in the art. For example, the vehicle may be any air, space, land, or water-based personal equipment or vehicle; any air, space, land, or water-based commercial equipment or vehicle; any air, space, land, or water-based military equipment or vehicle known in the art. For instance, the vehicle may include, but is not limited to, an automobile, a bus, a truck, a recreational vehicle (RV), a trailer, or the like. By way of another example, the personal aircraft seat air treatment system 124 and/or components of the personal aircraft seat air treatment system 124 including, but not limited to, the one or more treatment components 200 may be coupled to and/or configured to operate with an apparatus sold for commercial or industrial use in either a home or a business. Therefore, the above description should not be interpreted as a limitation on the present disclosure but merely an illustration.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

What is claimed:

1. A personal aircraft seat air treatment system, comprising:
    an air blower, the air blower being configured to receive cabin air from a cabin air ventilation system installed in an aircraft cabin, the cabin air including a mixture of recirculated air from inside the aircraft cabin and fresh air from outside the aircraft cabin;
    at least one ventilation output component installed within a passenger compartment, the at least one ventilation output component being configured to provide treated air to at least one breathing area of a passenger, the at least one breathing area being proximate to an aircraft seat installed in the passenger compartment; and
    at least one treatment component fluidically coupled to the air blower and the at least one ventilation output component, the at least one treatment component being configured to receive at least a portion of the cabin air from the air blower and treat the at least a portion of the cabin air to generate the treated air;
    the at least one treatment component comprising a hydrogel cartridge, the hydrogel cartridge being configured to generate humidified air from the cabin air by humidifying the at least a portion of the cabin air received from the air blower via dehydration of the hydrogel cartridge.

2. The air treatment system of claim 1, the at least one treatment component comprising an air purifier.

3. The air treatment system of claim 2, the air purifier including an ultraviolet germicidal irradiation lamp, the ultraviolet germicidal irradiation lamp being configured to generate the treated air from the cabin air by treating the at least a portion of the cabin air received via the air blower with ultraviolet light.

4. The air treatment system of claim 2, the at least one ventilation output component including a plurality of ventilation output components, a first subset of the plurality of ventilation output components being fluidically coupled to the air purifier and configured to receive the treated air from the air purifier, a second subset of the plurality of ventilation output components being configured to receive at least a second portion of the cabin air.

5. The air treatment system of claim 2, the at least one ventilation output component including a plurality of ventilation output components, each ventilation output component of the plurality of ventilation output components being fluidically coupled to the air purifier and configured to receive the treated air from the purifier.

6. The air treatment system of claim 1, the hydrogel cartridge being configured to be housed within a cannister, the cannister being fluidically coupled to the air blower and the at least one ventilation output component.

7. The air treatment system of claim 6, the cannister including a main body and a cannister lid, the hydrogel cartridge being removable from the main body when the cannister lid is disengaged.

8. The air treatment system of claim 1, further comprising:
    an air mixer, the air mixer being configured to combine the humidified air and at least a second portion of the cabin air to generate the treated air.

9. The air treatment system of claim 1, the one or more ventilation output components comprising a nozzle.

10. The air treatment system of claim 9, the nozzle being positioned within a head rest, a seat back, or a seat pan of the aircraft seat.

11. The air treatment system of claim 1, further comprising:
    an output blower, the output blower being configured to receive the treated air and provide the treated air to the at least one breathing area of the passenger.

12. An aircraft cabin, comprising:
    a cabin air ventilation system, the cabin air ventilation system being configured to generate cabin air, the cabin air including a mixture of recirculated air from inside the aircraft cabin and fresh air from outside the aircraft cabin; and
    a passenger compartment including an aircraft seat and a personal aircraft seat air treatment system, the personal aircraft seat air treatment system comprising:
        an air blower, the air blower being configured to receive the cabin air from the cabin air ventilation system;
        at least one ventilation output component installed within the passenger compartment, the at least one ventilation output component being configured to provide treated air to at least one breathing area of a passenger, the at least one breathing area being proximate to the aircraft seat installed in the passenger compartment; and
        at least one treatment component fluidically coupled to the air blower and the at least one ventilation output component, the at least one treatment component being configured to receive at least a portion of the cabin air from the air blower and treat the at least a portion of the cabin air to generate the treated air;
        the at least one treatment component comprising a hydrogel cartridge, the hydrogel cartridge being configured to generate humidified air from the cabin air by humidifying the at least a portion of the cabin air received from the air blower via dehydration of the hydrogel cartridge.

13. The aircraft cabin of claim 12, the passenger compartment further comprising:
    a control device, the control device including one or more processors and memory, the memory being configured to store a set of program instructions, wherein the one or more processors are configured to execute the program instructions to adjust one or more parameters of the personal aircraft seat air treatment system; and one or more sensors, the one or more sensors being configured to monitor at least one of rate of airflow or air quality through the personal aircraft seat air treatment system, the one or more sensors being communicatively coupled to the control device.

* * * * *